US008274276B2

(12) United States Patent
Kreutzbruck et al.

(10) Patent No.: US 8,274,276 B2
(45) Date of Patent: Sep. 25, 2012

(54) SYSTEM AND METHOD FOR THE NON-DESTRUCTIVE TESTING OF ELONGATE BODIES AND THEIR WELDBOND JOINTS

(75) Inventors: Marc Kreutzbruck, Berlin (DE); Gunnar Eidmann, Karlstein (DE); Kai Allweins, Schenklengsfeld (DE); Roland Mattheis, Jena (DE)

(73) Assignees: European Advanced Superconductor GmbH & Co. KG, Hanau (DE); Bundesanstalt fuer Materialforschung und-pruefung (BAM), Berlin (DE); Institut fuer Photonische Technologien E.V., Jena (DE)

( * ) Notice: Subject to any disclaimer, the term of this patent is extended or adjusted under 35 U.S.C. 154(b) by 924 days.

(21) Appl. No.: 12/282,488

(22) PCT Filed: Mar. 9, 2007

(86) PCT No.: PCT/EP2007/002102
§ 371 (c)(1), (2), (4) Date: Nov. 11, 2008

(87) PCT Pub. No.: WO2007/104497
PCT Pub. Date: Sep. 20, 2007

(65) Prior Publication Data
US 2009/0167298 A1 Jul. 2, 2009

(30) Foreign Application Priority Data

Mar. 10, 2006 (DE) .......................... 10 2006 011 281
Apr. 7, 2006 (DE) .......................... 10 2006 016 537

(51) Int. Cl.
*G01B 7/30* (2006.01)
*G01N 27/82* (2006.01)
(52) U.S. Cl. .................................. 324/207.25; 324/242
(58) Field of Classification Search ............. 324/207.25
See application file for complete search history.

(56) References Cited

U.S. PATENT DOCUMENTS

| | | | | |
|---|---|---|---|---|
| 5,073,744 | A * | 12/1991 | Buhler | 315/8 |
| 6,492,808 | B1 * | 12/2002 | Sukhorukov et al. | 324/242 |
| 6,504,363 | B1 | 1/2003 | Dogaru et al. | |
| 6,822,443 | B1 | 11/2004 | Dogaru | |
| 2002/0163333 | A1 * | 11/2002 | Schlicker et al. | 324/242 |
| 2005/0007108 | A1 | 1/2005 | Dogaru | |
| 2005/0189947 | A1 * | 9/2005 | Haugland | 324/338 |
| 2007/0244388 | A1 * | 10/2007 | Sato et al. | 600/424 |

FOREIGN PATENT DOCUMENTS

EP 1267161 A2 12/2002

OTHER PUBLICATIONS

English-Translation of the IPRP dated Oct. 23, 2008.

(Continued)

*Primary Examiner* — M'Baye Diao
(74) *Attorney, Agent, or Firm* — Sughrue Mion, PLLC

(57) ABSTRACT

An arrangement for testing an elongated body 1 or a welded and bonded joint in the body for faults 60 has a device 4, 5 for production of an eddy current in the elongated body 1 or its welded and bonded joint. At least one magnetic field sensor 7 for sensing the magnetic field is provided on the elongated body 1 or the welded and bonded joint. The dimensions of the at least one magnetic field sensor 7 are equal to or less than the fault 60 to be investigated.

19 Claims, 19 Drawing Sheets

OTHER PUBLICATIONS

K. Allweins et al., "Defect detection in aluminum laser welds using an anisotropic magnetoresistive sensor array", Journal of Applied Physics 97, pp. 10Q102-10Q102, XP012070091, 2005.

B. Wincheski et al., "Deep flaw detection with giant magnetorestrictive (GMR) based self-nulling probe", Review of Progress in Quantitative Nondestructive Evaluation 509, pp. 465-472, XP009083857, 2000.

C.H. Smith et al., "GMR magnetic sensor arrays for NDE eddy-current testing", Review of Progress in Quantitative Nondestructive Evaluation 657, pp. 419-426, XP009083858, 2003.

M. Muck et al., "Non-destructive testing of niobium sheets for superconducting resonators using an LTS SQUID system", Physica C 368, pp. 96-99, XP004336188, 2002.

* cited by examiner

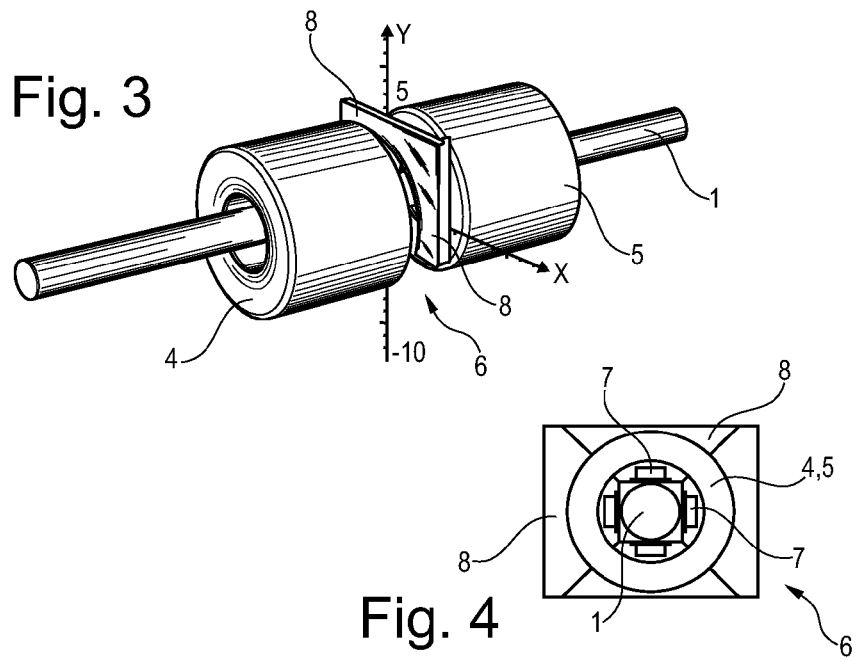
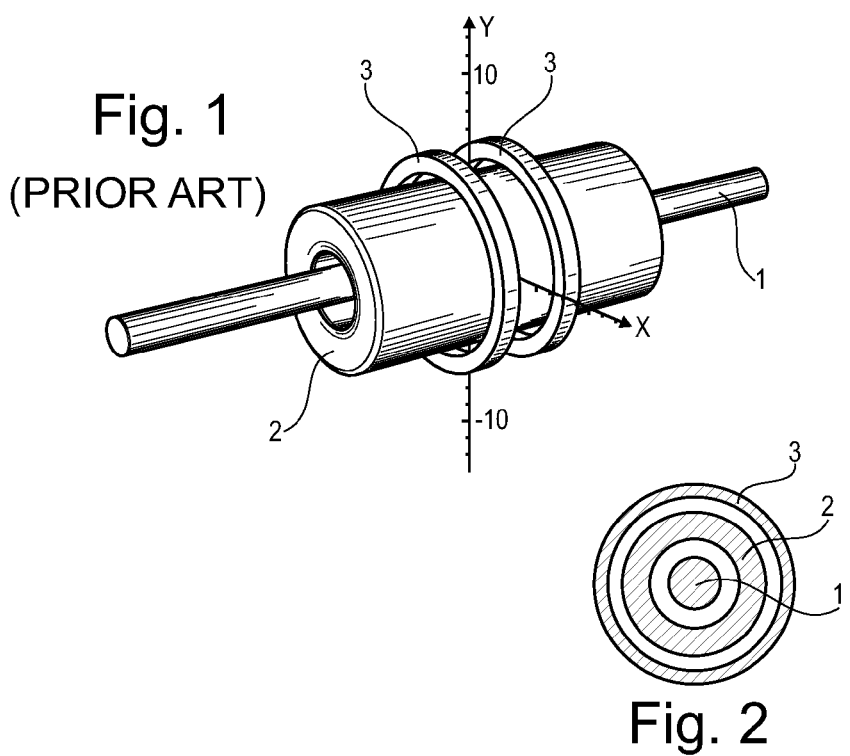

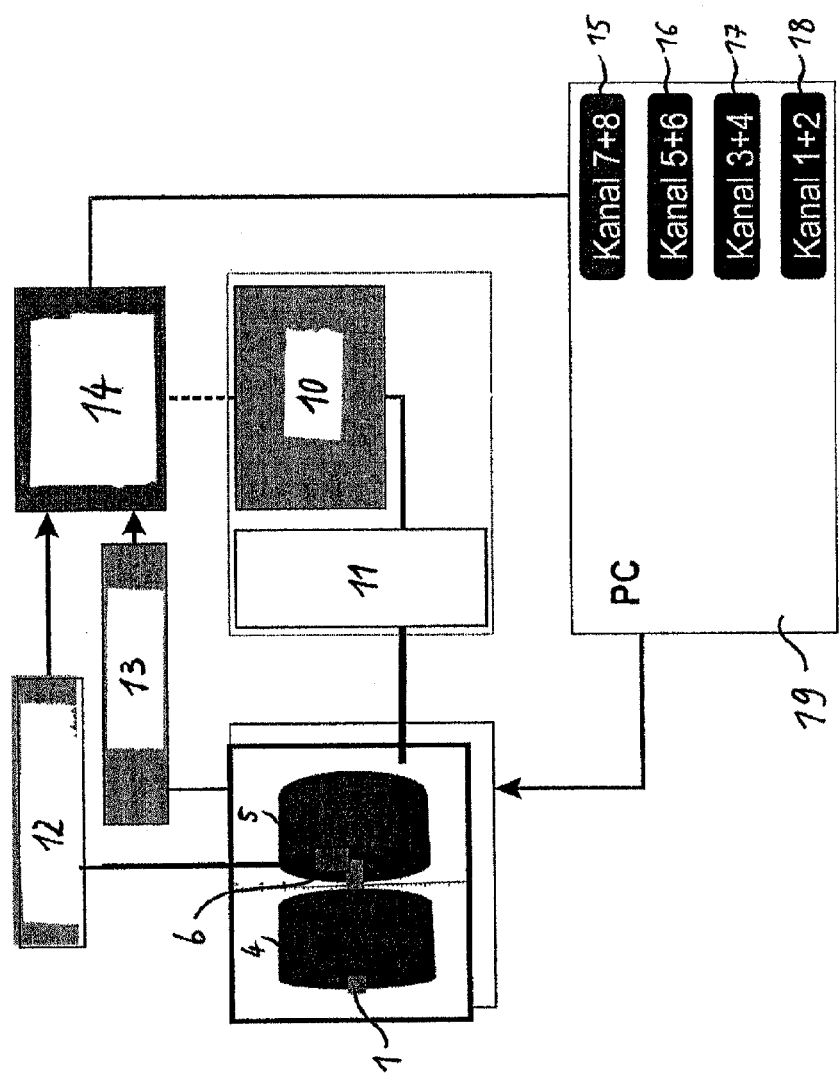

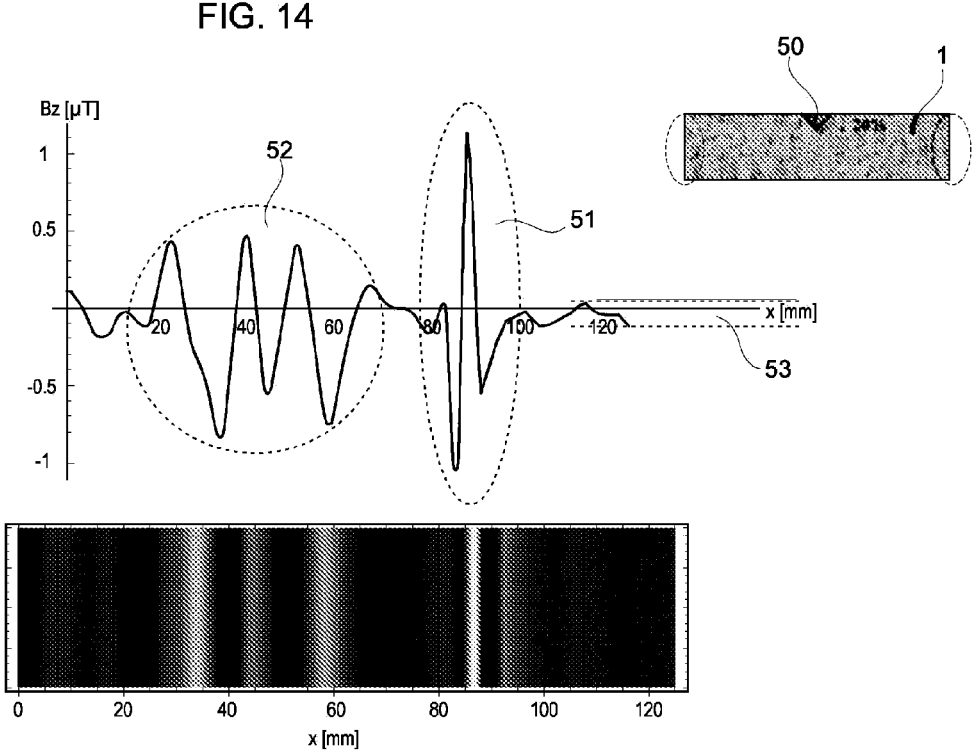

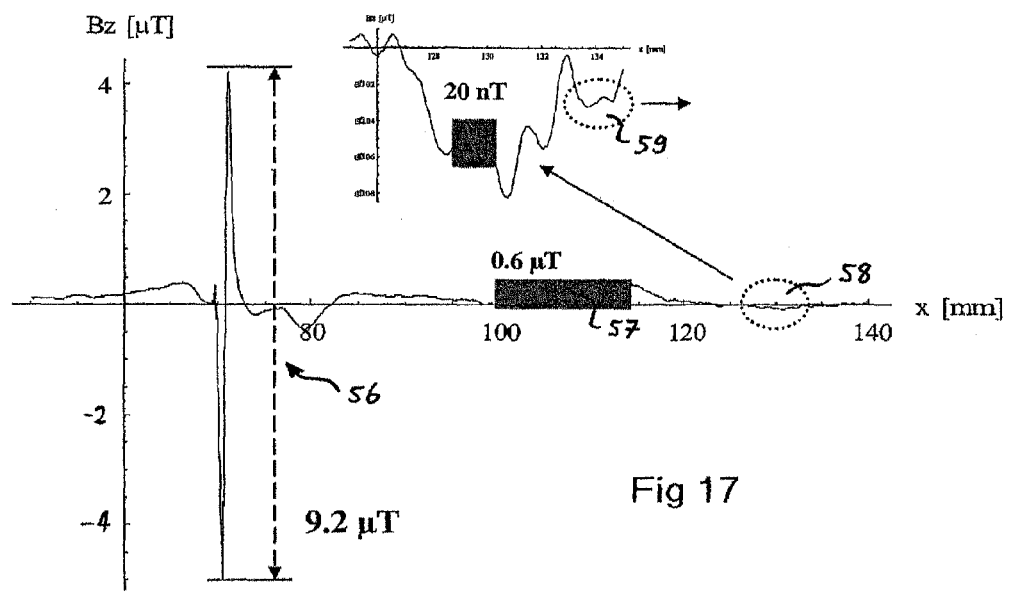

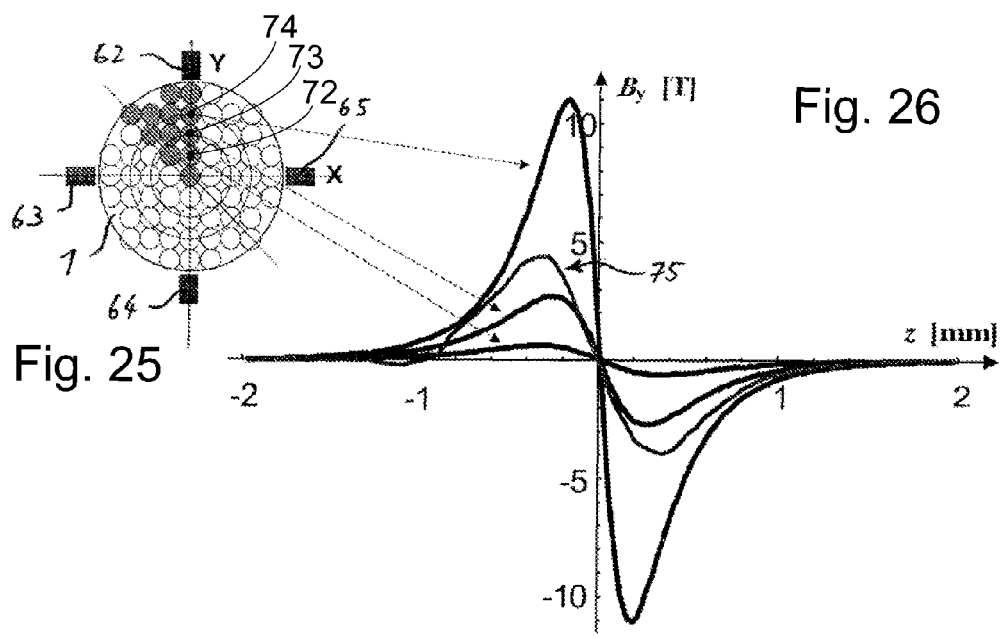
Fig. 25
Fig. 26
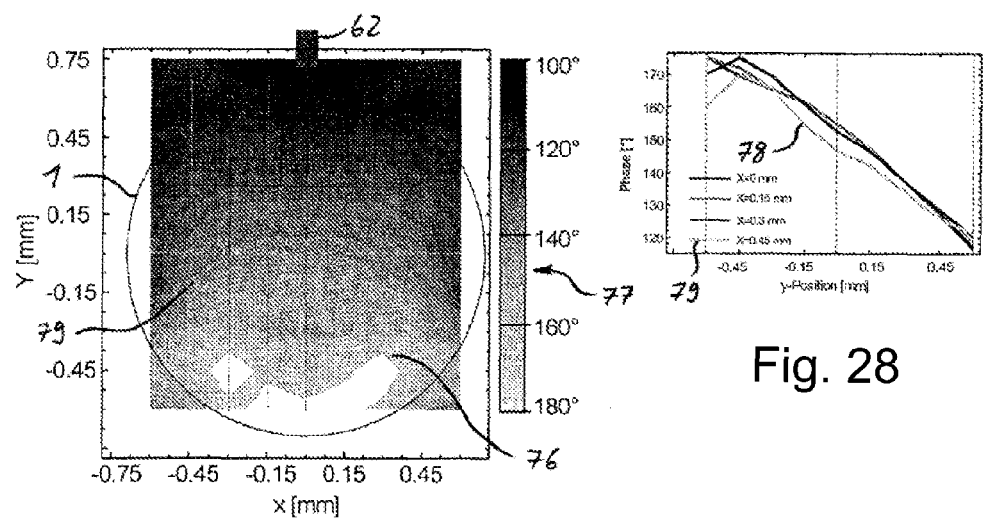
Fig. 27
Fig. 28

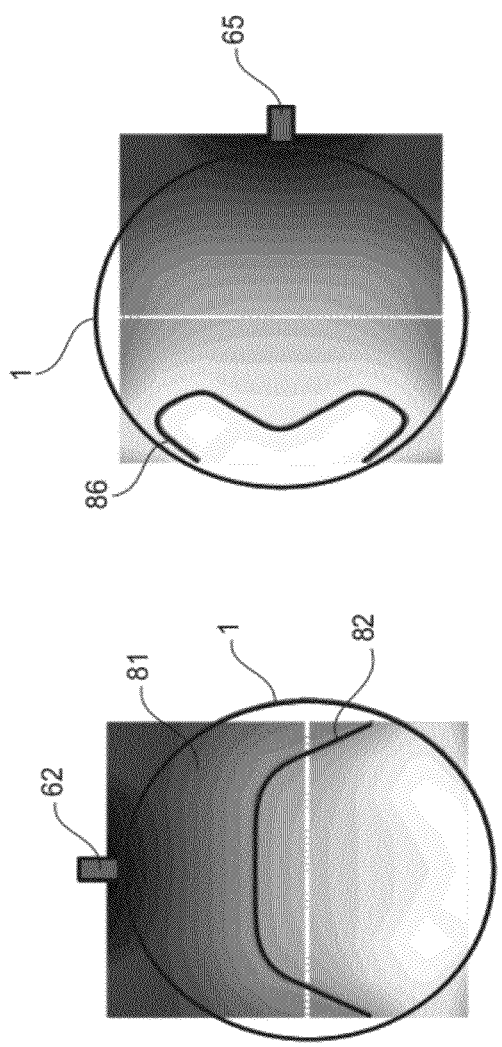

Fig 34
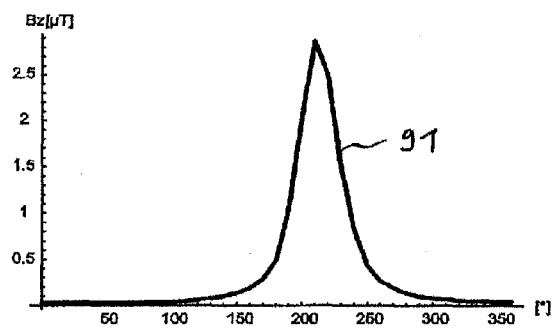
Fig 36
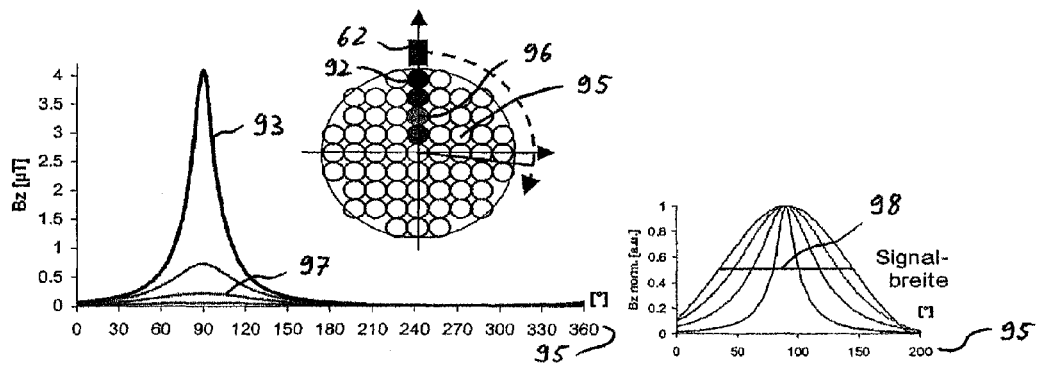
Fig 35          Fig 37

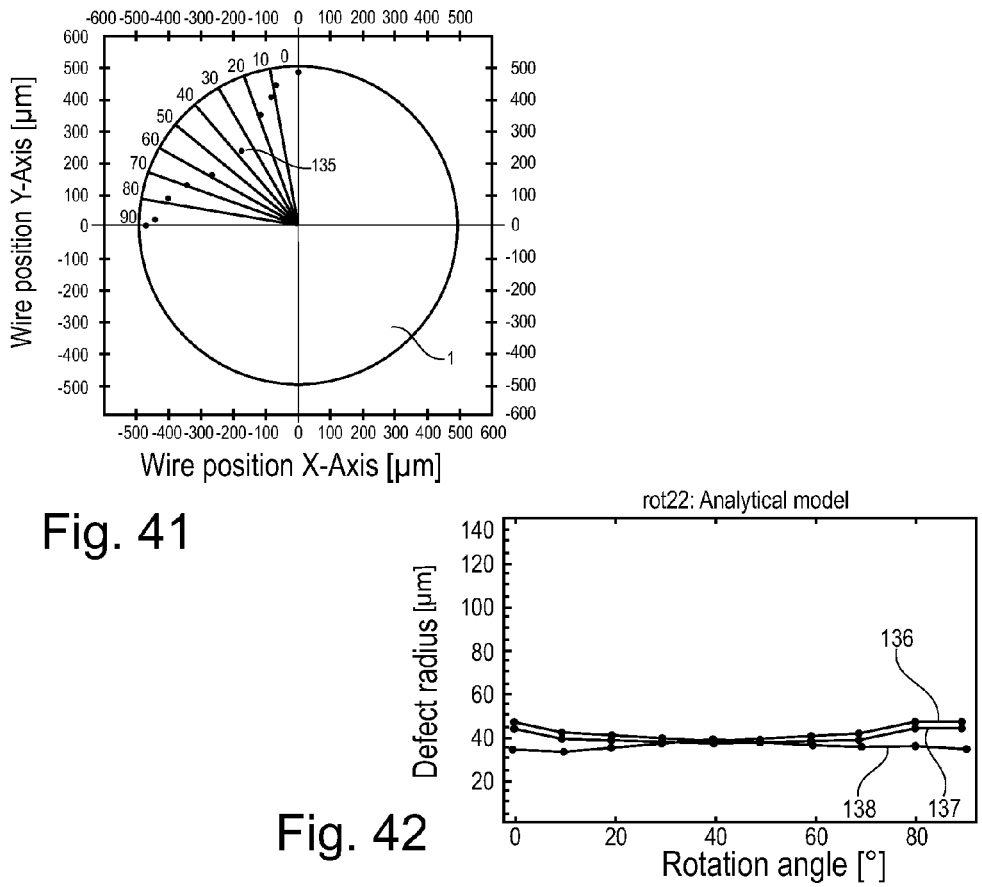
Fig. 41
Fig. 42
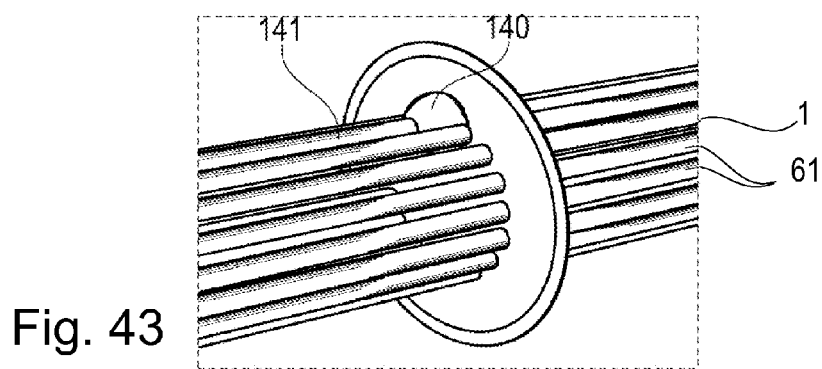
Fig. 43

SYSTEM AND METHOD FOR THE NON-DESTRUCTIVE TESTING OF ELONGATE BODIES AND THEIR WELDBOND JOINTS

The invention relates to an arrangement and method for testing elongated bodies, and their welded and bonded joints, which are electrically conductive or partially electrically conductive.

More stringent quality requirements (for example, ISO 9000 et seq) have resulted in a range of new test methods being developed and established in the field of non-destructive material testing. Nevertheless, a range of problems exist in the field of quality assurance which can be solved only to a limited extent physically and technically or only with a high cost involved. This relates, for example, to the detection of microscopic defects in aluminum welded beads and to the detection of defects in the production of aluminum bonding wires.

FIG. 1 shows a conventional eddy-current test arrangement. A wire 1 to be tested runs coaxially with respect to the longitudinal axis of an elongated excitation coil 2. Two detection coils 3 are arranged coaxially around the excitation coil 2. FIG. 2 illustrates a cross section through the arrangement shown in FIG. 1. The excitation coil 2 produces a magnetic field in the wire 1 and this leads to an eddy current in the wire 1. The eddy current caused by the excitation coil 2 itself produces a magnetic field in the wire 1, which induces a current in the detection coils 3. The induction current is measured and evaluated as a measure of the eddy current produced in the wire.

This has the disadvantage that the annular area of each detection coil 3 must be at least as large as the cross-sectional area of the excitation coil 2. The annular area of the detection coil is thus large in comparison to the cross-sectional area of the wire 1. The spatial resolution of the detection coil decreases as the annular area increases. The large annular area of the detection coils 3 is therefore associated with low spatial resolution. Defect signatures of the detected current of defects below the surface of the wire are in this case frequently similar to those of surface faults. The arrangement shown in FIGS. 1 and 2 does not produce very valid test results for the wire 1.

The field sensitivity of the detection coils 3 is low in comparison to the magnetic field changes to be measured, which are caused by normal defects in the wire. A strong excitation magnetic field is therefore required to produce a measurement signal which can be evaluated from the detection coils 3. This has the disadvantage that a strong magnetic field can be achieved only with excitation coils with a large extent, and this reduces the spatial resolution of the detection coils (see the statements in the last paragraph). The strong magnetic field for excitation can be superimposed on the weak magnetic field to be detected from the eddy current. The excitation magnetic field is then a "disturbance field" with respect to the magnetic field to be measured. This field reduces the sensitivity of the detection coils 3.

In order to locate and determine the size of an enclosure in the wire, a back-calculation method has, for example, been used until now, based on the phase and amplitude information of the demodulated measurement signal. Alternatively, magneto-sensor systems have also been used for high-sensitivity measurement of magnetic fields. In comparison to the conventional test arrangement illustrated in FIGS. 1 and 2, magneto-sensor systems allow more reliable detection of 100 μm large defects in electrically conductive test parts for excitation frequencies of up to 40 kHz [M. Mück, F. Gruhl, C. Welzel, M. von Kreutzbruck, Physica C 368, 96-99 (2002)].

Approaches have been adopted for the use of magneto-resistive (MR) sensors in non-destructive material testing [W. Ricken, J. Liu, W. J. Becker, EMSA 2000, Dresdner Beiträge zur Sensorik 13, 71-72 (2000)], [C. H. Smith, R. W. Schneider, T. Dogaru, S. T. Smith, Rev. Prog. in QNDE, 22, 419-426, (2003)], [B. Wincheski, M. Namkung, Rev. Prog. Quant. Non-destr. Eval. 509, 465 (2000)]. AMR sensors (Anisotropic Magneto Resistance) and GMR sensors (Giant Magneto Resistance) are suitable for many applications for non-destructive material testing because of a high spatial resolution with high field sensitivity. If a spatial resolution of 100 μm is required, field sensitivities of considerably better than 1 nT/√Hz can be achieved using MR sensors. From the remaining pool of magneto-sensors, only SQUID sensors (Superconducting Quantum Interference Device) also offer a higher field sensitivity with the same spatial resolution, but this can be achieved only with a large amount of hardware complexity and at high financial cost.

The object of the invention is to improve the non-destructive detection of faults in elongated bodies as well as welded and bonded joints, without significantly increasing the effort or cost.

The object is achieved by an arrangement as claimed in claim 1, and by a method as claimed in claim 41.

A measurement and test arrangement is provided in which a current is produced in the wires or microcontacts, in order to test wires and microcontacts. This is based on the assumption that faults in the wires or microcontacts have a conductivity which differs from that of the wire or microcontact. The current produced in the body to be tested therefore flows around the fault to be detected and flows to a greater extent through it in comparison with the body surrounding the fault. The magnetic field caused by the current flow in the body to be tested is sensed by at least one magnetic field sensor. The magnetic field sensor is approximately the same size as the fault or faults to be investigated or is even smaller than it or them. A device can be used which produces a magnetic field that passes through the body to be tested. The magnetic field produces eddy currents in the body to be tested, whose magnetic fields are then likewise sensed by at least one magnetic field sensor.

The magnetic field sensors have magneto-resistive (MR) sensor elements which are approximately the same size as the fault to be examined or are smaller than it. The spatial resolution of the high-sensitivity magneto-resistive sensor elements is approximately in the same order of magnitude as the dimensions of the fault or faults to be investigated.

By way of example, microcontacts to be tested may be welded or bonded joints. The body to be tested is composed of electrically conductive or electrically partially conductive materials. The material may be in the form of a pure substance, alloy or composite material with or without insulation. Furthermore, the body to be tested may be a superconductor or semi-finished product on which an eddy-current test method can be used for the production of superconductors. The body to be tested may comprise a ceramic high-temperature superconductor or a metallic superconductor. It is also possible for the body to be tested to have a combination of a metallic and a ceramic superconductor.

High-precision determination of the position and size of faults can be achieved by means of magnetic field sensors which are opposite with respect to the cross-sectional center point of the elongated body. Ratios of variables are evaluated, which are formed from amplitudes of magnetic fields of mutually opposite magnetic field sensors. The position and size of a fault can be determined just by two magnetic field sensors using signals which are initiated by the fault. The two sensors are arranged outside the body to be tested on a cross-sectional plane of the body to be tested, with the sensors forming an angle of 90° radially.

If four sensors are arranged in an annular form around the body to be tested with the same separations between the sensors on the circumference of the body, the measured values of the signals from in each case two sensors can be related to one another. Six signal ratios can be formed. Two of the signal ratios are formed by the magnetic field amplitudes of mutually opposite magnetic field sensors. The four further signal ratios are formed from the magnetic field amplitudes of sensors which are adjacent on the circumference of the body to be tested. If four magnetic field sensors are arranged in an annular form around an elongated body, this results, with six signal ratios, in an overdefined system for determination of the position and size of the fault to be investigated. The position and size of the fault can be determined, therefore, even if one or more of the four magnetic field sensors is or are not producing an adequate signal for measurement of a fault. The position and size of a fault can only be estimated on the basis of the signal from only one of the four magnetic field sensors.

AMR (Anisotropic Magneto Resistance) or GMR (Giant Magneto Resistance) sensors may be used as magneto-resistive sensors. An array comprising a multiplicity of XMR (AMR, GMR) sensors is likewise possible. By way of example, an AMR array comprising 64 individual sensors may be used, with each individual sensor having a permalloy strip. The field sensitivity of each individual sensor may be approximately 1 nT/√Hz. Each individual sensor in the array of 64 sensors may have a size of 50·20 $\mu m^2$ and may be at a distance of 350 µm from its adjacent sensors. If the distance between each individual sensor and the body to be tested is 100 µm±10 µm, the spatial resolution is 100 µm±10 µm.

As an alternative to an AMR sensor array with an overall length of, for example, 26.8 mm, GMR sensors can be arranged in an annular form around the body to be tested, on the cross-sectional plane of the body.

The invention will be explained in more detail in the following text with reference to the examples illustrated in the figures. Unless stated to the contrary, the same reference symbols in the figures denote the same components with the same meaning.

FIG. 1 shows a schematic view of a conventional eddy-current test arrangement with an excitation coil and two detection coils;

FIG. 2 shows a cross section through the eddy-current test arrangement shown in FIG. 1;

FIG. 3 shows a schematic view of a test arrangement with two excitation coils and four magnetic field sensors;

FIG. 4 shows a cross section through the test arrangement shown in FIG. 3;

FIG. 5 shows a schematic illustration of the test layout of an arrangement for eddy current testing;

FIG. 14 shows, in the form of a graph, a measurement signal of a multidefect structure and of a reference notch in a wire;

FIG. 15 shows a visualization of the measurement data from FIG. 14 in the form of a brightness pattern;

FIG. 17 shows, in the form of a graph, measurement data of an inclusion in a wire;

FIG. 18 shows, in the form of a graph, measurement data of a signal, which is not caused by a fault, in the measurement data shown in FIG. 17;

FIG. 25 shows, schematically, a cross section through a wire with pores, with four magnetic field sensors being arranged around the wire;

FIG. 26 shows, in the form of a graph, signal strengths calculated by means of FEM, for pores at different positions in the wire as shown in FIG. 25, as well as measurement data of an inclusion in the wire as shown in FIG. 25;

FIG. 27 shows a visualization of phase information in a brightness pattern relating to a measured air pore in a wire;

FIG. 28 shows, on the basis of a diagram, the phase information from FIG. 27 in the y-direction, originating from four positions in the x-direction;

FIG. 29 shows a visualization of a phase band in a brightness pattern relating to measurement data, which is caused by a fault, from a magnetic field sensor which is positioned at the upper end of a wire;

FIG. 30 shows a visualization of a phase band in a brightness pattern relating to measurement data caused by a fault, from a magnetic field sensor positioned at the side of a wire;

FIG. 31 shows a visualization of a phase band in a brightness pattern relating to measurement data caused by a fault, from a magnetic field sensor positioned at the lower end of a wire;

FIG. 32 shows an illustration of a cross section through a wire with superimposed phase bands, which are shown in FIGS. 29 to 31 and which form an intersection as a position of the fault;

FIG. 34 shows, in the form of a graph, measurement data of a signal shift resulting from an inclusion in a wire, as a function of the angle position of the measuring sensor with respect to the inclusion;

FIG. 35 shows an illustration in the form of a graph of simulated defect signatures as a function of the angle between a magnetic field sensor and a fault, for various positions of the fault;

FIG. 36 shows, schematically, a cross section through a wire, with faults which cause measured values as shown in FIG. 35 in the wire;

FIG. 37 shows, in the form of a graph, the simulated defect signatures as shown in FIG. 35 with normalized signal strengths;

FIG. 41 shows, with respect to the wire cross section, measurement data of positions calculated back from a fault for different angle positions of the fault with respect to the sensors in a test arrangement with four sensors;

FIG. 42 shows, in the form of a graph, the radius of a fault calculated from the positions of the fault shown in FIG. 41, for three magnetic field sensors;

FIG. 43 shows, three-dimensionally, a current distribution which is calculated by means of FEM in a superconducting wire with a defect zone and thick core;

Figure 45:
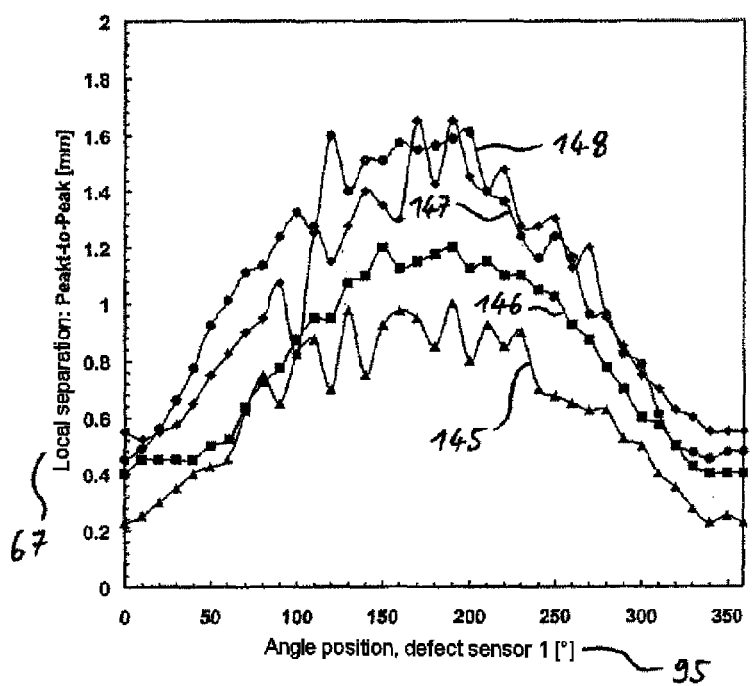
Figure 46:
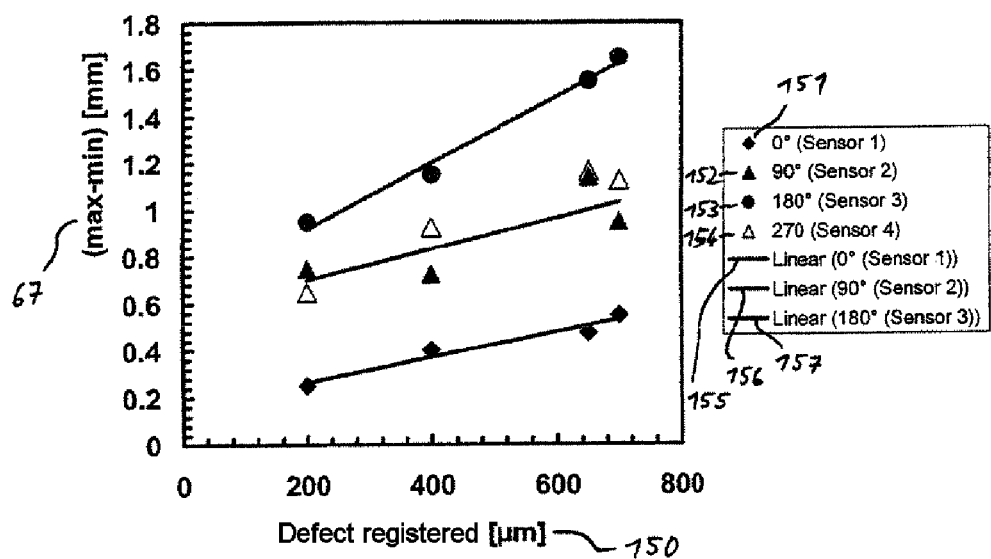

FIG. 45 shows an illustration in the form of a graph of signal lengths of defect signals for four different wires as a function of the angle position of the defect with respect to the sensor; and FIG. 46 shows an illustration in the form of a graph of signal lengths of the defect signals for four magnetic field sensors which are arranged in the form of a ring around a wire, as a function of the defect length for a defect angle position of 0°.

An arrangement for eddy current testing of a wire 1 is illustrated in FIG. 3. The wire may have a diameter of greater than or equal to 10 μm. The diameter of the wire is preferably between 0.5 and 2 mm. The faults to be detected in the wire 1 preferably amount to 5 to 10% of the diameter of the wire 1. The expression defect is used in the following text as an alternative to the expression fault. A defect means a body with a limited spatial extent which is located in the body to be investigated. A defect may be a deformation or a foreign body in the body to be investigated. A combination of deformation and body is likewise possible as a defect. Deformation which affects only the outside of the body to be investigated but does not change the functionality of the body is not a defect. For example, scratches on an outer insulating layer on a wire are not defects, provided that they do not adversely affect the operation of the insulating layer.

Excitation coils 4, 5 are used to produce an eddy current in the wire 1 as the body to be tested. Alternatively, the eddy current can be produced in the wire 1 solely by the earth's magnetic field. The body to be tested must be composed of electrically conductive or partially electrically conductive materials. These may be in the form of a pure substance, an alloy or a composite material with or without insulation. Superconductors and semi-finished products on which a current test method can be used, for the production of superconductors, are also suitable for testing. In particular, tests can be carried out on ceramic high-temperature superconductors or metallic superconductors. A combination of a ceramic superconductor and a metallic superconductor is also possible.

In the arrangement as shown in FIG. 3, two toroidal coils are provided as excitation coils 4, 5. The test layout, which is also referred to as the test equipment, comprises the excitation coils and the detection array 6. The toroidal coils each define a plane, with the wire 1 running at right angles to the planes of the coils along the longitudinal axis of the coils. The body to be tested runs at right angles to the planes of the four toroidal coils, through the center points of the coils. The wire 1 is moved relative to the test equipment. The relative velocity between the body to be tested and the test equipment may be up to 100 m/s.

The excitation coils may be in the form of "gradiometric excitation coils". If the toroidal coils 4, 5 are arranged in a gradiometric form the excitation magnetic field at the location of the detection array 6 is very largely compensated for. For example, gradiometric excitation coils produce a magnetic field of ±0.5 mT in the wire 1. The toroidal coils 4, 5 may be at a distance of a few mms from one another.

As an alternative to toroidal coils, double-D coils can also be used as excitation coils 4, 5. By way of example, when using double-D coils, the detection array 6 may comprise an AMR sensor array. The AMR sensor array can be positioned parallel between the two halves of the excitation coil. The magnetic excitation field at the location of the AMR sensor array between the semicircles of the double-D is less by a factor of about 200 than the maximum field of the double-D coil. The arrangement comprising double-D coils and AMR sensor array 6 arranged parallel to these coils is particularly suitable for measurement of microdefects. By way of example, an AMR sensor array with an overall length of 26.8 mm is used for measurement of welded and bonded joints. Each of the 64 individual sensors in the AMR array has a size of 50×20 μm$^2$ and is at a distance of 375 μm from its adjacent sensors. Each individual sensor comprises a permalloy strip and has a field sensitivity of approximately 1 nT/√Hz.

The detection array 6 may also comprise four segments 8 that are joined together. Each segment 8 comprises a magnetic field sensor 7. The excitation magnetic field at the location of the magnetic field sensors 7 is reduced by a factor of about 3 in comparison to the maximum field within the coils 4, 5. The positioning accuracy of each magnetic field sensor 7 with respect to the elongated wire 1 is, for example, less than or equal to the magnitude of ±10 μm. High positioning accuracy can be achieved by a manipulator (not shown). A manipulator is a unit which can be moved on one or more axes. The movable unit comprises at least one electric motor or hydraulic motor. The motor is controlled outside the movement unit. One magnetic field sensor 7 can in each case be fitted to the manipulator. When the magnetic field sensor 7 is positioned with high accuracy with respect to the wire 1 it is possible for the magnetic field sensor 7 to be at a distance from its desired position from the wire 1. Each magnetic field sensor may be offset laterally with respect to the axis of symmetry of the wire 1. Inaccuracies in the positioning of the magnetic field sensor with respect to the body to be tested can be produced in particular by bending of the body to be tested and/or by oscillation of the body. The test arrangement shown in FIG. 3 allows the magnetic field sensors 7 each to be arranged with an accuracy of less than or equal to 10 µm with respect to their desired positions.

FIG. 4 shows a cross section through the detection array 6 illustrated in FIG. 3. Each magnetic field sensor 7 has a spatial resolution of between 60 and 120 µm. The four magnetic field sensors 7 are arranged in the form of a ring at equal distances from one another on the circumference of the wire 1 at a distance of 100 µm±10 µm from the wire 1. The four sensors form a plane which runs at right angles to the wire direction. Two magnetic field sensors are in each case located opposite one another with respect to the center point of the wire. The wire 1 runs at right angles to a plane which is formed by the ring of magnetic field sensors, through the center point of the ring. The wire 1 is arranged coaxially with respect to the longitudinal axis of the excitation coils 4, 5.

In the present case, by way of example, AMR sensors 7 with a magnetic field sensitivity of approximately 1 nT/√Hz are used. These sensors make it possible to locate faults reliably in the body 1 to be tested or in its welded and bonded joint with a size between, for example, 100 µm and 750 µm.

FIG. 5 shows the layout of a test arrangement for an eddy current test. A function generator 10 produces a sinusoidal alternating current which is required for excitation. The alternating current is amplified in an output stage 11 and feeds the excitation coils 4, 5.

Magnetic fields produced by the excitation coils induce eddy currents in the wire 1. The detection array 6 senses the magnetic fields produced by the eddy currents in the wire 1. A read unit 12 passes the magnetic field signals from the detection array 6 to a multichannel lock-in amplifier 14. The lock-in amplifier uses a compensation signal 13, which originates from the function generator, to demodulate the magnetic field signals caused by faults and defects. The multichannel lock-in amplifier 14 makes it possible to read a plurality of individual sensors in the detection array 6 simultaneously.

By way of example, a multichannel lock-in amplifier with 16 channels is used simultaneously to read a plurality of individual sensors of a detection array 6. By way of example, eight sensors in a line array, which form a central part of the line array can be read for eddy current measurements on weld beads. In addition, a further eight sensors are read. These sensors are arranged at an increasing distance from an adjacent sensor to the left and right of the sensors in the central part of the line array, over the entire width of the line array. This allows a weld bead and its relatively close surrounding area to be sensed with a single line scan. The optimum excitation frequencies for the sheet-metal thicknesses used are determined before the measurement by means of a finite element simulation (FEM). For example, a suitable excitation frequency for an aluminum sheet with a thickness of 1 mm is 20 kHz.

Eight channels are preferably used for the multichannel lock-in amplifier 14 in order to read two channels of a magnetic field sensor in each case when using four magnetic field sensors. The simultaneous sensing of more than four sensors, for example 8, 16 or 24 sensors, is likewise possible by means of the lock-in amplifier 14 with an appropriate number of available measurement channels. The spatial resolution for the fault to be investigated increases with the number of different signals produced by a fault. In addition to amplitude information, the lock-in amplifier 14 also provides phase information or real and imaginary parts of the sensed magnetic fields.

GMR sensors can achieve higher field sensitivities than AMR sensors. The achievable field sensitivities with a GMR sensor may have values of up to 200 pT/√Hz. GMR sensors can also be combined to form arrays in the same way as AMR arrays. By way of example, the magnetic fields which can be measured by GMR arrays are between 1 pT and 10 pT. The test layout illustrated in FIGS. 3 to 5 can achieve high repetition accuracies in the comparison of measurement data relating to different measurements which are produced by a fault. If the data from individual measurements is compared with the averaged measurement data, the relative measurement discrepancy is between 3 and 5%. The signal-to-noise ratio (SNR) for the sensed magnetic field of faults in an elongated body is, for example, between 7 and 2000. The signal strength of the magnetic field caused by the faults is in this case between 10 and 30 nT.

The output signals from the lock-in amplifier 14 are evaluated in an evaluation unit 19. By way of example, a GMR sensor is used as a sensor. In addition to the amplitudes, the evaluation unit 19 processes the phase angle of the output signal with respect to the reference excitation. The distance between a minimum and a maximum in an output signal can also be evaluated and is referred to as the signal length. The phase angle, amplitude, signal length and the number of peak values in the measured values of the lock-in amplifier 14 are characteristics of a fault in the body to be tested. The evaluation unit 19 can identify characteristic features of a fault, can isolate them from the rest of the measurement data and can read them, that is to say sense them in a form that allows them to be extracted. An estimate of the minimum and maximum number of damaged filaments in an elongated body with a filament structure is part of the characteristic features. In good measurement conditions, the discrepancy between the minimum and maximum value is no more than 50% of the true value. Good measurement conditions occur when the body to be investigated is measured with virtually no vibration, with a sensor positioning accuracy of approximately ±50 µm. The back-calculation algorithm of the evaluation unit 19 allows a spatial resolution of 0.5 mm in the longitudinal direction of the body to be investigated to be achieved with the body to be investigated moving through the test arrangement at a maximum speed of 5 m/s. If the diameter of the body to be investigated is 1 mm, the spatial resolution on the cross-sectional plane of the body to be investigated is approximately ±50 µm. The spatial resolution is scaled linearly with the respective diameter of the elongated body to be investigated, for example in a diameter range from 0.4 to 6 mm. The evaluation unit 19 makes it possible to make a decision to stop the machine during continuous measurement at a maximum speed of 5 m/s in less than 30 ms. Within this time period, the test layout shown in FIG. 5 transmits a signal to the control system for the machine that is being used to test and possibly produce the body to be investigated.

Figure 6:
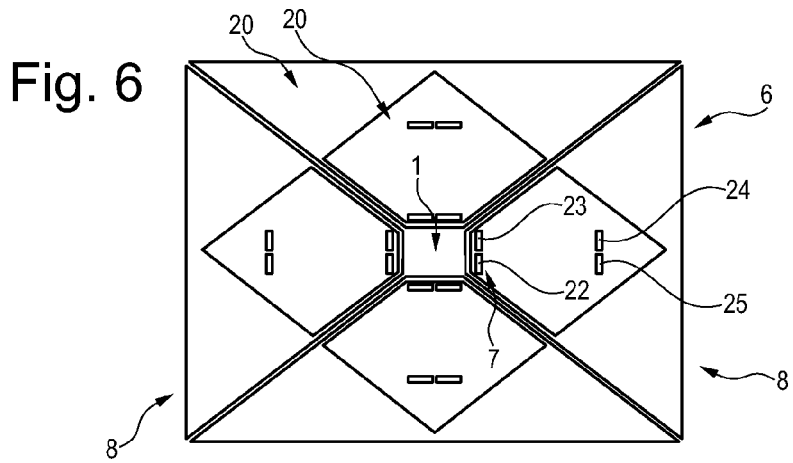
FIG. 6 shows a schematic illustration of an arrangement of four magnetic field sensors around a wire.

FIG. 6 shows, schematically, an arrangement of four magnetic field sensors around a wire. The detection array 6 comprises four sensor segments 8. Each sensor segment 8 has a chip 20 with four GMR sensors 22, 23, 24, 25. The chip 20 is located on a board section 21. The sensor segments 8 each have a shape which runs to a point in the direction of the wire 1 to be investigated. The GMR sensors 22 to 25 on a sensor segment 8 are used to form a Wheatstone bridge circuit. Each sensor segment 8 represents a position-resolving magnetic field sensor. The arrangement as shown in FIG. 6 of four magnetic field sensors arranged in the form of a ring around a wire makes it possible to find the position of faults in the wire with an accuracy of, for example, 5 to 10% of the diameter of the wire.

Figure 7:
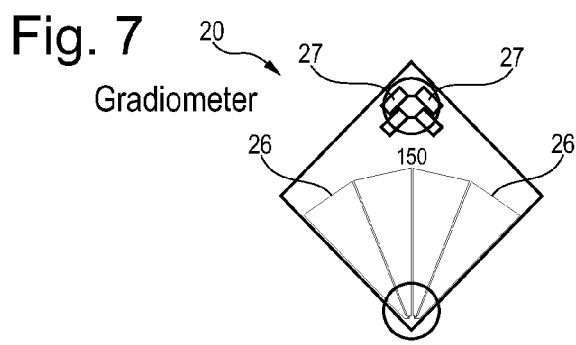
FIG. 7 shows a schematic illustration of a magnetic field sensor in the form of a gradiometer chip.

A schematic illustration of a magnetic field sensor in the form of a gradiometer chip 20 is shown in FIG. 7. Four aluminum bonding pads 26 are applied to the chip 20 in a meandering shape, located close to one another and electrically isolated from one another. Aluminum bonding pads 27 are located at the upper end of the chip 20. The chip area is about 4.3×4.3 mm².

Figures 8, 9:
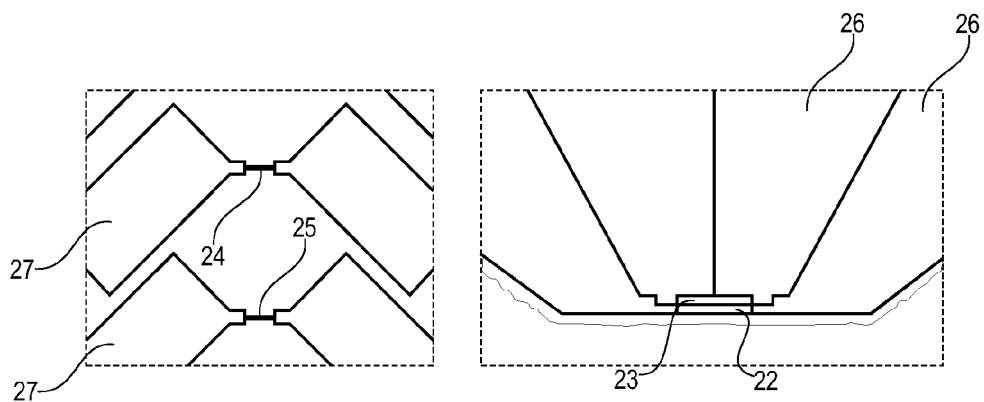
FIG. 8 shows a microscopic photograph of two resistance strips at the upper end of the gradiometer chip shown in FIG. 7.
FIG. 9 shows a microscopic photograph of two resistance strips at the lower chip edge of the gradiometer chip shown in FIG. 7.

FIG. 8 shows a microscopic photograph of two resistance strips 24, 25 at the upper end of the gradiometer chip 20. The resistance strips 24, 25 each have a length of 150 μm and a width of 9 μm.

FIG. 9 shows a microscopic photograph of two resistance strips 22, 23 on the lower chip edge of the gradiometer chip 20. The corner of the chip in FIG. 9 is approximately 30 μm in front of the resistance strips 22, 23. The resistance strips 22, 23 are GMR sensors which sense magnetic field signals with high spatial resolution. If the faults in the body to be examined or in its welded and bonded joint have a size between 100 μm and 750 μm, the magnetic field sensors are approximately the same size as the faults to be investigated, or are smaller than them.

Figure 10:
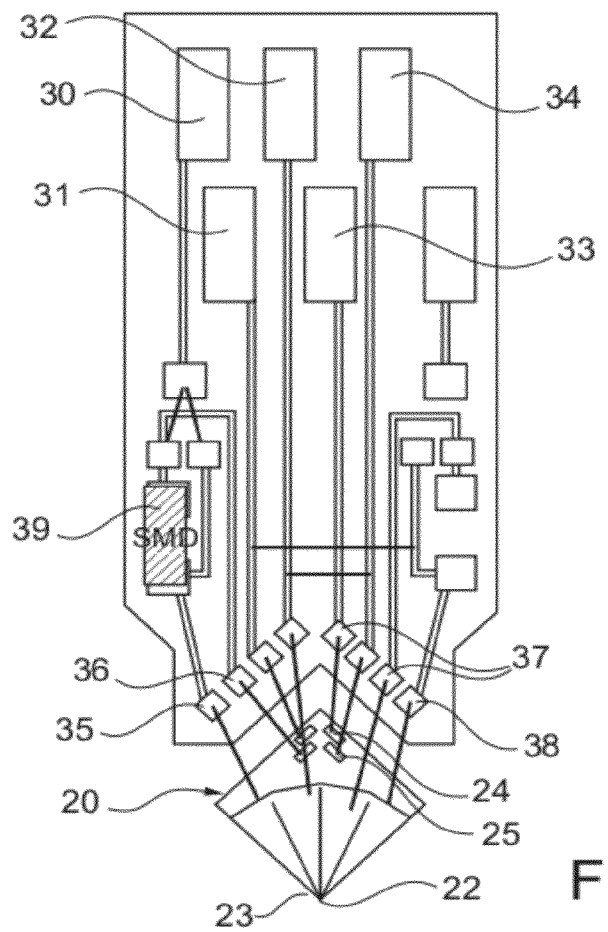
FIG. 10 shows a plan view of the board layout of the gradiometer chip shown in FIG. 7 for a Wheatstone bridge circuit.

FIG. 10 shows, schematically, a board layout of the gradiometer chip 20 with a Wheatstone bridge circuit. In order to suppress the disturbing influence of temperature-dependent fluctuations on the sensed magnetic fields and to suppress magnetic field variations with a range which is considerably greater than the size of the chip 20, four resistance strips 22 to 25 are combined in a Wheatstone bridge circuit. The four resistance strips form a common magnetic field sensor. The chip 20 is bonded to a ceramic substrate, with bonding wires connecting the aluminum bonding pads 26 to contact pads 35 to 38. The bonding wires are encapsulated in epoxy resin for example. The contact pads 35 to 38 are connected to further contact pads 30 to 34 via conductor tracks.

Figure 11:
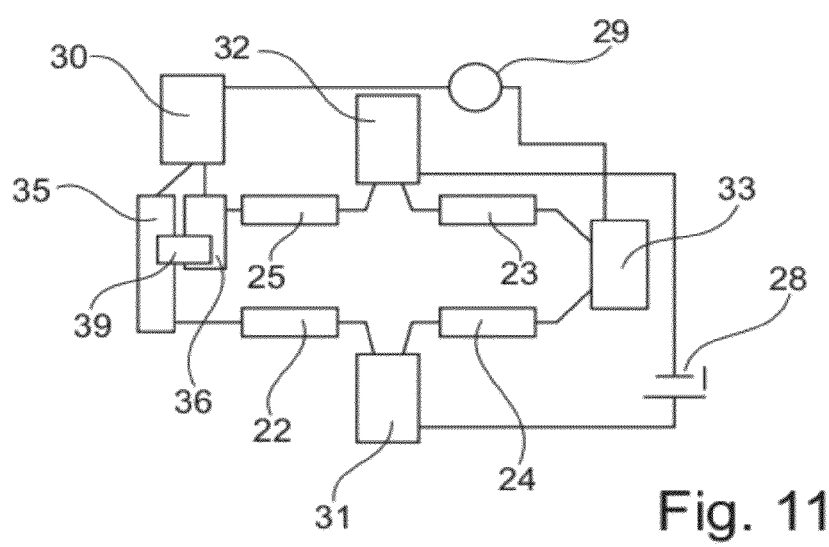
FIG. 11 shows the equivalent circuit of the board layout shown in FIG. 10.

FIG. 11 illustrates an equivalent circuit of the board layout shown in FIG. 10. The GMR resistance strips 22 to 25 form a Wheatstone bridge circuit. The Wheatstone bridge is supplied with a voltage 29 at the contact pads 30, 33. The signal taps for the bridge are the contacts 31, 32. The bridge is balanced by means of a resistor 39. By way of example, the value of the resistor 39 is 47-56Ω. The resistor 39 may be in the form of a surface-mounted device (SMD) resistor. The balancing resistor 30 is included in the appropriate half-bridge arm by means of a bonding wire. The balancing resistor 39 can be adjusted by tapping off either at the upper end of the resistor 39 or at the lower end of the resistor 39.

Figure 12:
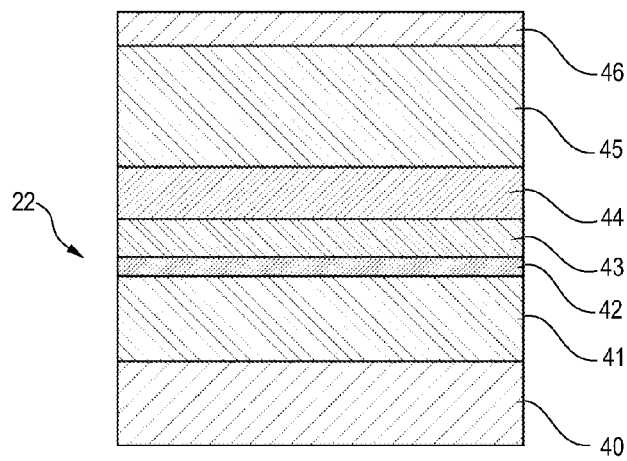
FIG. 12 shows a cross section through a GMR layer stack.

FIG. 12 shows, schematically, the layout of a GMR layer stack as a cross section through the GMR resistance strip 22. The layer stack 22 comprises a tantalum layer 40, with a width of 5 nm, as a growth layer. The functional layers which follow one another are a permalloy (nickel-iron) layer 41 with a width of 5 nm, onto which a cobalt-iron layer 42 with a width of 1 nm is applied as a sensor layer. Furthermore, a copper layer with a width of 2.2 nm or 3.5 nm is applied as an intermediate layer 43. A cobalt-iron layer 44 with a width of 3 nm is located above this, to which an iridium-manganese layer 45 with a width of 7 nm is applied as a reference layer. The layer stack 22 is closed by a ruthenium layer 46 with a width of 2 nm as a covering layer in order to protect the stack.

Figure 13:
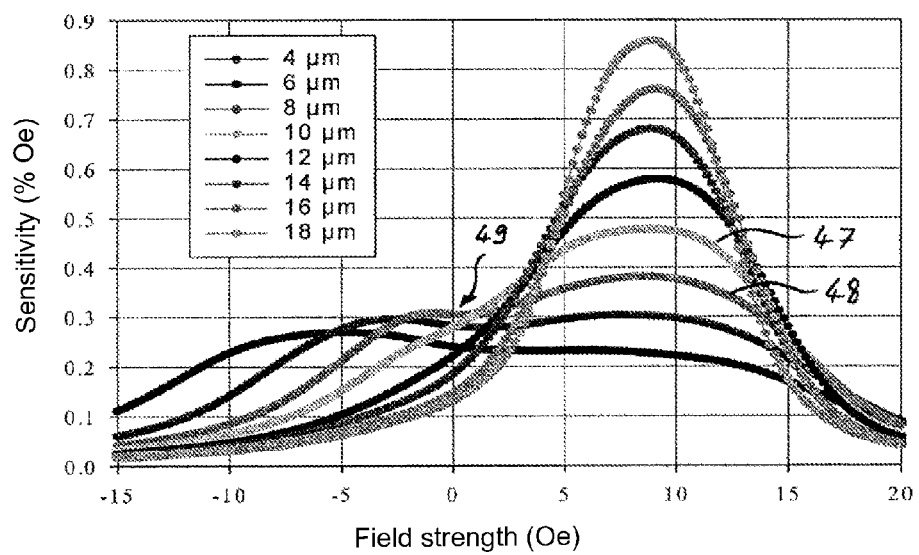
FIG. 13 shows, in the form of a graph, the field sensitivity of the layer stack from FIG. 12 with a 2.5 nm thick copper layer.

The graph in FIG. 13 shows the field sensitivity of the layer stack 22 as a family of curves with the copper layer 43 having a thickness of 2.5 mm. The family of curves comprises eight curves, with each curve representing a different strip width of the layer stack 22. The sensitivity is the resistance change as a percentage of the magnetic field strength in Oersted. The maximum sensitivity when no external field is present occurs at 0.4%/Oe (49) for a web with a length of 600 μm, with a web width of 8 μm (48) and 10 μm (47).

FIG. 14 shows a measurement signal of a multidefect structure 52 in a wire 1 in comparison to the measurement signal 51 of a reference notch 50. The reference notch 50 has a depth of 20% of the diameter of the wire 1 measured from the wire surface in the direction of the wire axis. The diameter of the wire 1 for the measurements in FIG. 14 is 1.3 mm. The excitation frequency is 10 kHz. The measurement data relating to the sensed magnetic fields originates from four GMR sensors, which are arranged in the form of a ring around the wire, on a cross-sectional plane of the wire. In addition to the clear signals from the reference notch 51 and the multidefect structure 52, a noise region 53 can be seen in FIG. 14. The fault in the wire 1 can be detected clearly even with the raw data 52. FIG. 15 shows a visualization with a brightness pattern of the measurement data 51, 52.

Figure 16:
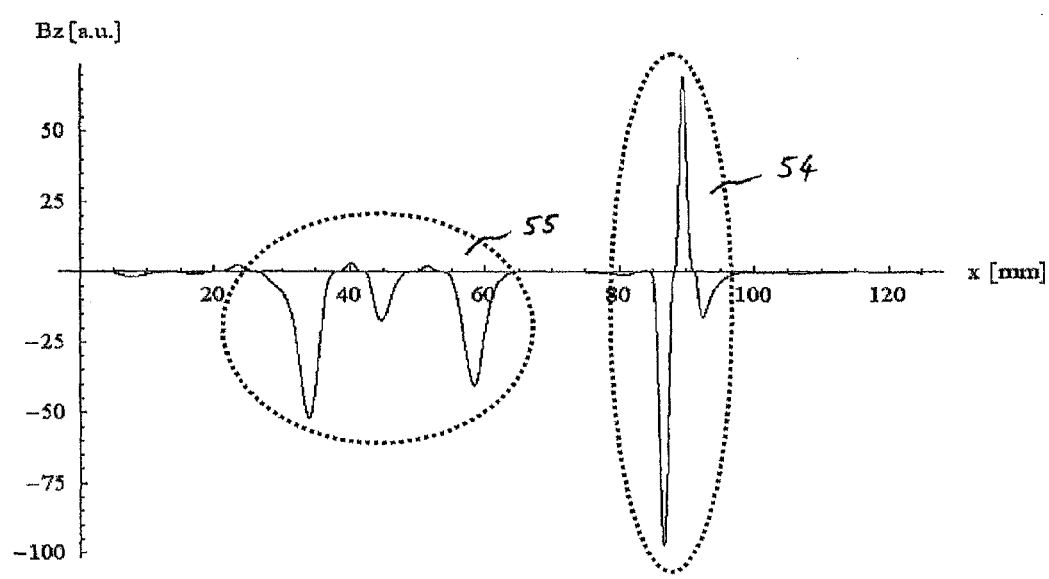
FIG. 16 shows the measurement data from FIG. 14 after signal processing.

A further improvement in the signal-to-noise ratio can be achieved by suitable signal processing. The measurement data from FIG. 14 is illustrated, after signal processing, in FIG. 16. In comparison to the noise 53 in the measurement data in FIG. 14, the noise in the measurement data 54, 55 in FIG. 16 is considerably reduced. The signal processing comprises, for example, the following steps:

Compensation for the movement of the wire 1 at right angles to the longitudinal axis of the wire 1. The compensation is carried out by subtraction of a linear function of the measurement data relating to the sensed magnetic fields. The measurement data is set to zero by subtraction of the linear function.

Setting the phase angle in the sensed magnetic field via a phase rotation until the sensed magnetic field of the fault in one channel has an amplitude which is as large as possible in comparison to a compensation signal. Amplitude and phase data which are sensed in the lock-in amplifier 14 are used.

Compensation for the joint movement of the elongated wire 1 in the direction of the axis of the wire 1 by squaring the sensed magnetic field or a variable which is formed from the sensed magnetic field.

FIG. 17 shows a measurement of an inclusion with a diameter of 1.3 mm in a wire. The excitation frequency is 10 kHz. The measured defect signature has a signal shift, that is to say a distance between the maximum and minimum of 9.2 μT (56). In addition to the useful signal resulting from a fault in the wire, the measurement in FIG. 17 also includes artifacts of about 0.6 μT (57) and 20 nT (58). An artifact is a measurement signal which is not caused by a fault to be investigated. The artifact of 0.6 μT (57) is caused by discrepancies in the wire from a straight shape. This artifact occurs in the case of wires which have been wound up and then straightened. The artifact 57 has no influence in industrial use.

The artifact of about 20 nT (58) is illustrated in the form of a graph in FIG. 18. This artifact is caused by minor discrepancies in the surface topology of the wire from an ideal wire surface (scratches, etc.). The artifact 58 can also be caused by vibration of the wire. Vibration occurs, for example, when starting/braking the movement unit by means of which the wire is moved through the test arrangement.

Figure 19:
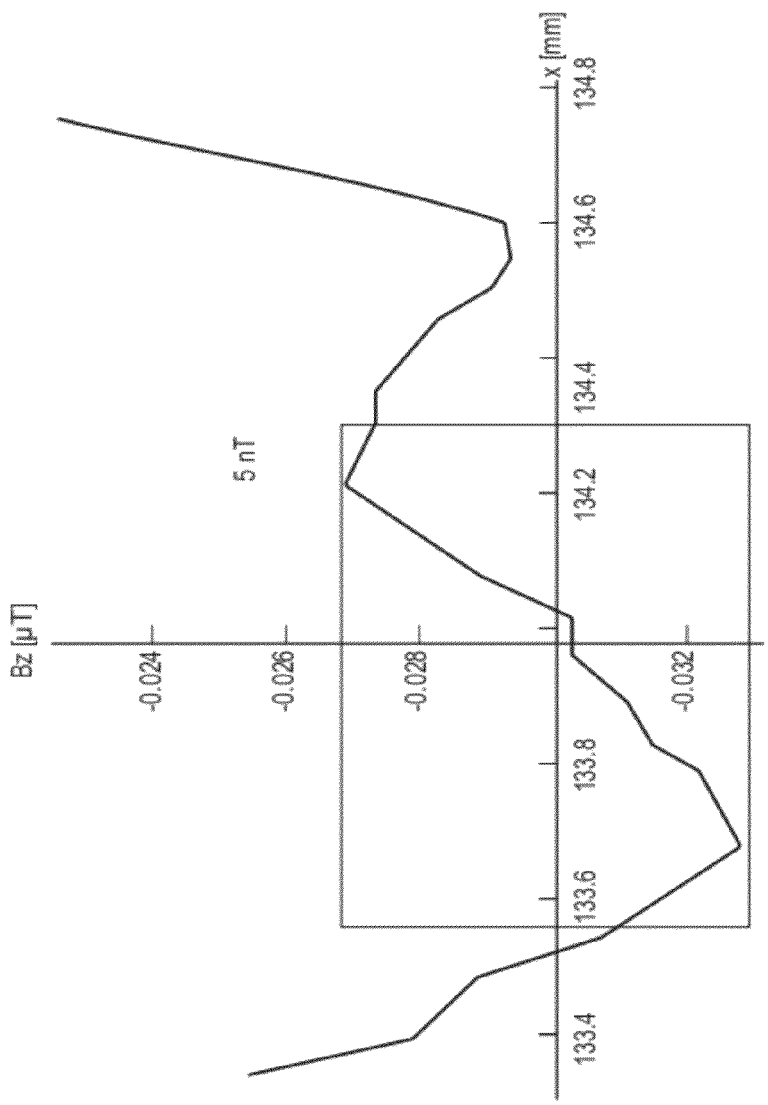
FIG. 19 shows, in the form of a graph, measurement data of a signal which is not caused by a fault, in the measurement data shown in FIG. 16.

FIG. 19 shows, enlarged, an area 59 from FIG. 18. An artifact with a signal shift of 5 nT can be seen. This artifact is caused by system noise, which results from the processing electronics. The noise of the GMR sensor by means of which the measurement data in FIGS. 17 to 19 is produced is below 1 nT/√Hz.

If the disturbance signal strength for the measurements shown in FIG. 17 is assumed to be 20 nT, then this results in a signal-to-noise ratio of 460. Measurements of larger defects than those measured in FIG. 17 lead to an SNR of more than 1000.

Figure 20:
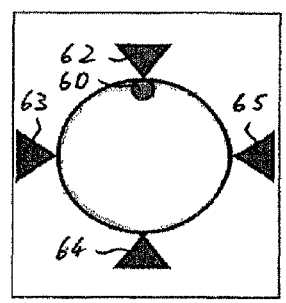
FIG. 20 shows, schematically, the cross section through a wire which has a fault and four magnetic field sensors arranged in an annular form with respect to it.

The arrangement for measurement of faults is shown schematically in FIG. 20. 4 GMR sensors 62 to 65 are arranged in the form of a ring around the wire and on the cross-sectional plane of the wire. The operating frequency for the measurement is 10 kHz, and the speed of movement of the wire 1 with respect to the measurement arrangement is 40 mm/s. The wire diameter of the wire 1 is 1.2 mm. The distance between the magnetic field sensors and wire surface is between 50 μm and 100 μm. The defect 60 moves past underneath the magnetic field sensor 92.

Figure 21:
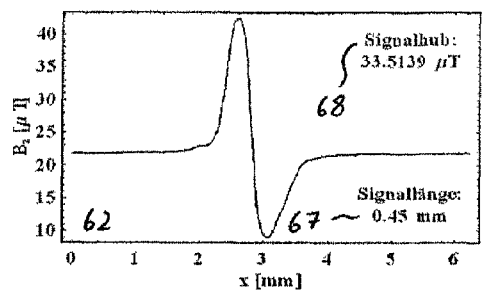
FIG. 21 shows, in the form of a graph, a measurement signal which is caused by a fault, at the magnetic field sensor directly above the fault.
Figure 22:
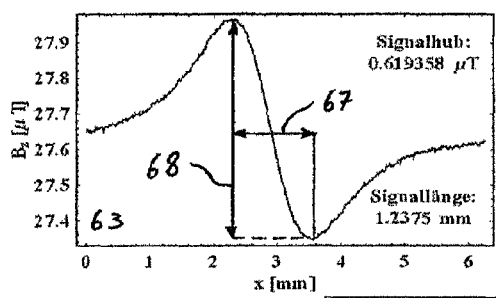
FIG. 22 shows, in the form of a graph, a measurement signal which is caused by a fault, from a magnetic field sensor which is at an angle of 90° with respect to the fault.
Figure 23:
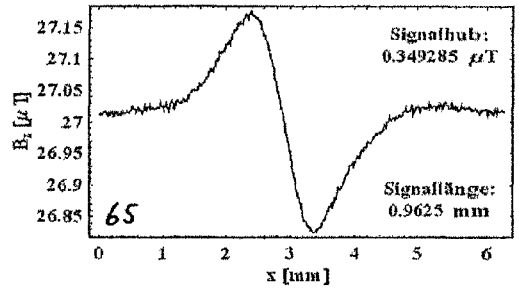
FIG. 23 shows, in the form of a graph, a measurement signal which is caused by a fault, from a second magnetic field sensor which is at an angle of 90° to the fault.
Figure 24:
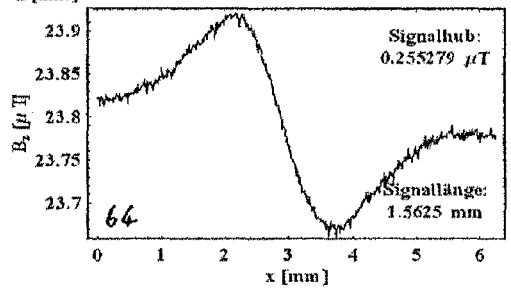
FIG. 24 shows, in the form of a graph, a measurement signal which is caused by a fault, from a magnetic field sensor opposite the fault.

FIG. 21 illustrates, in the form of a graph, the measurement signal relating to the fault 60 which was sensed directly above the fault 60 by means of the magnetic field sensor 62. The signal shift 68 is about 33 μT with a signal length 67 of 0.45 mm. FIGS. 22 and 23 show the measurement signals from the sensors 63 and 65. With respect to the fault 60, the magnetic field sensors 63 and 65 are inclined through 90° with respect to the fault, on the cross-sectional plane of the wire. FIG. 24 shows an illustration in the form of a graph of the magnetic field measurement of a fault 60 by means of the magnetic field sensor 64. The sensor 64 is located on the side of the wire 1 opposite the position of the fault 60. As expected, the sensor 64 which is furthest away from the fault 60 produces the least signal shift 68. The signal shift of the measured signal of the sensor 64 is approximately two orders of magnitude less than the signal shift of the measurement signal from the sensor 62. One conspicuous factor in the measurement data from the magnetic field sensors 62 to 65 is that the signal length 67 increases as the distance from the defect 60 increases.

Defects with a short extent in the direction of the wire axis have shorter signal widths than defects with a long extent in the wire direction, for a given angle on a cross-sectional plane of the wire between the magnetic field sensor and the defect. Defects with a narrow extent at right angles to the direction of the wire axis result in a faster rise in the signal length 67 with increasing angle on the cross-sectional plane of the wire of the magnetic field sensor with respect to the fault than defects with a broader extent at right angles to the wire direction. This will be described further below, as well.

FIG. 25 illustrates schematically the cross section through a wire with 61 pores. Four magnetic field sensors 62 to 65 are arranged at equal distances from one another around the wire 1 and on the circumference of the wire. The wire diameter 70 is 1.425 mm. The excitation frequency is 10 kHz. The defect radius of each pore 72 to 74 is 75 μm. In order to locate defects in the interior of a wire 1 and to determine their size, a back-calculation algorithm is used in the evaluation unit 19. The back-calculation algorithm comprises a database. The position and size of a fault to be investigated are stored in the database as a function of the phase information and amplitude information of the demodulated measurement signal from the lock-in amplifier 14. The data in the database can be determined from a fusion of phase information and amplitude information from the demodulated measurement signal from the magnetic field sensors.

In order to derive the back-calculation algorithm, wires 1 with reference defects 72 to 74 are transferred to a finite element model. This is based on the assumption that a pore 72 to 74 is positioned at each of 61 positions within the otherwise homogeneous wire 1. In order to calculate a magnetic field signature of a fault 72, FIG. 25 shows the fault 72 arranged directly underneath the sensor 62.

FIG. 26 shows the amplitude strengths, calculated by means of FEM, for a respective fault 72 to 74 in the wire 1. The magnetic field signal, calculated by means of FEM, from the sensor 62 exhibits the greatest signal shift for the fault 72. The pore 73 is positioned closer to the axis of the wire 1 than the pore 72. A magnetic field signal from the sensor 62 is determined by means of FEM for the pore 73, and exhibits approximately half the signal shift of the fault 72. The pore 74 is positioned close to the axis of the wire 1. The magnetic field signal calculated by means of FEM for the sensor 62 for the pore 74 exhibits the smallest signal shift. The measurement sensitivity of the GMR sensor 62 that is used as the basis for the FEM calculation is sufficiently high also to determine defects in the vicinity of the center point of the wire 1 with an adequate signal-to-noise ratio (SNR).

One conspicuous feature in the curves in FIG. 26 is that the signal length 67 of the measurement signal increases as the distance between the fault and the magnetic field sensor carrying out the measurement increases. For comparison, FIG. 26 shows a magnetic field measurement for an inclusion with a defect radius of 65 μm (75). The signal form, signal shift and signal length of the measured magnetic field signal 75 result in a good match with the data calculated by means of the FEM method.

FIG. 27 shows brightness values 76 of phase information relating to a measured air pore in a wire 1. The phase is in a range between 100° and 180° (77). The data shown in FIG. 27 is calculated using an FEM simulation for a spherical air pore. The diameter of the air pore is 150 μm. The FEM simulation is also based on a wire diameter of 1.4 mm and an excitation frequency of 10 kHz. As the fault to be measured, the spherical pore has a negligible conductivity in comparison to that of the wire 1.

Because the conductivity of the pore is less than that of the wire 1, the eddy current which is produced in the wire 1 is diverted around the fault. The change in the magnetic field of the eddy current resulting from this is detected by the sensor 62 as a magnetic field signal. The pore to be measured in the wire 1 results in a change in the phase in the measurement signal from the sensor 62 in comparison to the reference excitation of 10 kHz, as well as resulting in a signal shift in the amplitude. The phase differences between a defect directly underneath the sensor 62 and a defect on the side opposite the wire center point depend on the diameter of the wire 1 and on the excitation frequency that is used. For example, a higher excitation frequency leads to a faster phase shift. The phase difference produced by the pore in FIG. 27 is 80° from the minimum (dark gray) to the maximum (white) of the phase on the scale 77.

The phase differences are illustrated in the form of a graph in FIG. 28 for the phase information from FIG. 27. The direction from the sensor 62 to the wire axis on the cross-sectional plane of the wire 1 defines the y-axis of the cross-sectional plane. The x-axis runs at right angles to the y-axis. The phase differences are plotted for four positions in the x-direction with respect to the reference excitation in the y-direction in FIG. 28. As the distance from the sensor 62 increases, the calculated phase difference increases continuously from about 120° to 180°, in comparison to the reference excitation.

The position of the defect to be measured in the wire can be derived from a so-called "phase band" from the phase differences, calculated by means of FEM, of a sensor 62. The position of the fault to be investigated is not defined unambiguously since the position of the fault may be located at any point in the phase band. The phase band in FIG. 27 corresponds to one brightness level and is formed from positions of equal phase on the cross-sectional plane of the wire on which the sensor 62 is located.

FIGS. 29 to 32 illustrate the process of determining the defect position via phase information from a plurality of magnetic field sensors. FIG. 29 shows a first phase band 82 for the phase information 80 from the magnetic field sensor 62, as a curved line. The position of the fault to be investigated is determined by superimposition of different phase bands from magnetic field sensors which are located at different positions outside the wire. A second phase band 86 of the phase information 85 from a sensor 65 is located on the right-hand outer edge of the wire as shown in FIG. 30. A further phase band 84 is shown in FIG. 31 for a sensor 64 which is opposite the sensor 62 with respect to the wire center point.

FIG. 32 shows, in the form of a cross section, the superimposition of the phase bands 82, 84 and 86 for determining the position of the fault. The position of the fault corresponds to the intersection 87 of the phase bands 82, 84 and 86. Superimposition of only the phase bands 82 and 86 from the sensors 62 and 65 results in two intersections 80, 83 in the immediate vicinity of the position of the fault. Superimposition of the phase bands 82 and 84 from the sensors 62 and 64 likewise results in two intersections 85, 87. The position of the fault to be investigated is determined uniquely by superimposition of phase bands of at least three magnetic field sensors at a distance from one another. When four magnetic field sensors are arranged in the form of a ring around a wire with equal distances between the sensors on the circumference of the wire, a defect can be located with an accuracy of, for example, 5 to 10% of the wire diameter.

The formation of the intersection 87 of the phase bands 82, 84 and 86 assumes the alignment of the phase angle of the phase bands with respect to one another and with respect to the wire 1. The alignment of each phase band 82, 84 and 86 with respect to the respective other phase bands 82, 84 and 86 and with respect to the body to be investigated, for example a wire, is carried out on the basis of the positions of the magnetic field sensors 62, 64, 65 with respect to one another and with respect to the body to be investigated.

It is likewise possible to determine the position of the fault using just the amplitude data from a plurality of sensors relating to a fault to be investigated. It is advantageous to arrange the sensors 62 to 65 on a ring at equal distances from one another on the circumference of the body 1 to be investigated. An intersection of two lines as the position of a fault can in this case be formed using the amplitudes from magnetic field sensors which are opposite the center point of the body to be investigated. The magnetic field component $B_z$, in the direction from the center point on the wire cross section to the respective sensor which is aligned toward the center point of the wire cross section, from a defect which is assumed to be in the form of a point, is inversely proportional to the distance z of the defect from the magnetic field sensor:

$$B_z(z) \sim \frac{1}{z^2} \quad (1)$$

Despite the fact that the magnetic field decreases with the square of the distance from the defect to be measured, it is possible to use one GMR sensor to measure a defect located at the opposite end of a wire (see FIG. 24). A better SNR ratio is achieved if sensed magnetic fields are evaluated from sensors which are opposite with respect to the axis of the body to be investigated. Test measurements show that the amplitude ratio of two opposite sensors is described best by a theory which takes account only of the projection onto the axis formed by the two sensors. Mutually opposite sensors thus register only the magnetic field component in the direction of the axis which is defined by the two sensors.

If the ratio of the amplitudes of mutually opposite sensors is formed, then the values that are formed correspond to amplitude bands which run at right angles to the axis formed by the sensors on the cross-sectional plane of the body to be investigated. The value for the amplitude ratio that is formed corresponds to a position of the fault to be investigated in the respective amplitude band relating to this value on the cross-sectional plane of the body to be investigated.

In order uniquely to determine the position of a defect, four sensors which are arranged around the body to be investigated can be arranged on a ring, in each case at equal distances from one another, on the circumference of the body. The sensors which are opposite the longitudinal axis of the body to be investigated form a sensor pair, which pair is offset with respect to the two further mutually opposite sensors through an angle of 90° on the cross-sectional plane of the body to be investigated. If the amplitude ratios are formed for each of the two sensor pairs which are offset through 90° with respect to one another, the values that are formed correspond to amplitude bands on the cross-sectional plane of the body to be investigated. These amplitude bands form a crosswire on the cross-sectional plane of the body to be investigated. The intersection of the crosswire corresponds to the position of the fault to be investigated.

The spatial resolution increases with the number of mutually opposite sensor pairs which are separated from one another by the same angular interval. It is therefore advantageous to use 8, 16 or 24 sensors instead of 4 sensors. The position of a fault can be determined unambiguously by means of at least four magnetic field sensors which are arranged around the body to be investigated, at equal distances from one another on the circumference of the body. The amplitude ratios of two respective sensors opposite the cross-sectional center point of the body to be investigated can be determined in this case. The position of a fault can also be determined when two magnetic field sensors which are opposite the center point of the body to be investigated are each offset with respect to one another in the direction of the longitudinal axis of the body to be investigated. The offset between the sensor pairs is compensated for in the evaluation unit 19 by inclusion of the relative velocity of the body to be investigated with respect to the sensors. In addition to forming the amplitude ratios of signals from mutually opposite sensors, it is possible to form the ratio of the amplitudes of sensors which are adjacent on the circumference of the body to be investigated.

Figure 33:
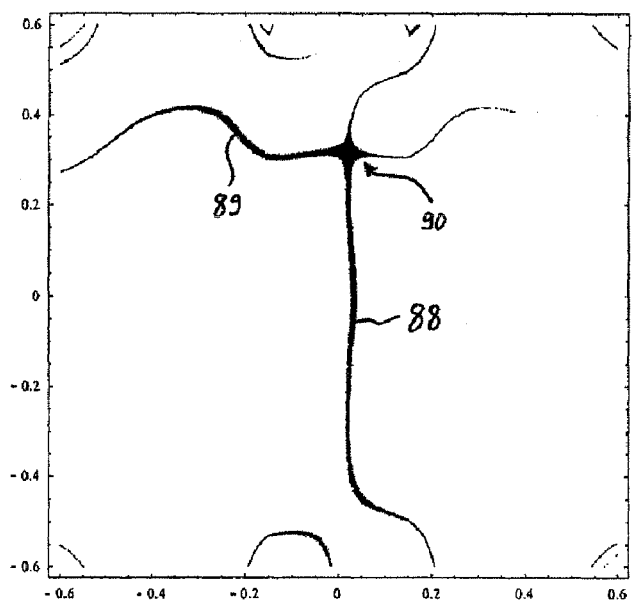
FIG. 33 shows a cross-sectional illustration of a wire with curved lines which are calculated on the basis of amplitude ratios of mutually opposite magnetic field sensors in a wire in an FEM simulation, and which form an intersection as the position of the fault.

FIG. 33 shows a cross section of an FEM simulation of amplitude ratios of mutually opposite magnetic field sensors in a wire. The wire diameter is 1.04 mm. The frequency of the exciting magnetic field is 10 kHz. The amplitude bands 88 and 89 which intersect at the intersection 90 each correspond to one value for an amplitude ratio. It is possible to determine the position of a defect for each amplitude ratio of two mutually opposite sensor pairs, from matching the amplitude ratios together with FEM simulations. The position of a defect depends on the frequency of the magnetic field, the position and the diameter of the fault to be investigated. The position of a fault to be investigated is also influenced by the material of the fault. For a given amplitude ratio, the position of the fault also depends on the diameter of the elongated body in which the fault to be investigated is located. The FEM simulations which are used to determine the position of a fault are therefore carried out as a function of the diameter of the elongated body with the fault to be investigated, the excitation frequency, the position, the diameter and the material of the fault.

The FEM simulation for determination of the position of a fault comprises a back-calculation algorithm which includes further physical effects of the measurement. The current density produced by a current that is fed in or by an external magnetic field is not constant within the elongated body. The current density of an eddy current decreases exponentially towards the center point of the wire. The current density of the eddy currents, which decreases exponentially towards the center point of the wire, is also included in the FEM simulation.

However, real defects are not in the form of points but have an extent which differs from that of a point. The eddy current density within the defect is therefore not constant. As stated, the magnetic field sensors register a magnetic field change which is caused by the change in the eddy current flow around a defect. Areas of the defect such as these produce a larger signal, because a higher eddy current density flows around them. These are the areas located outside a defect. Furthermore, extended defects lead to the measured magnetic field decreasing when the distance between the sensor and the defect is relatively long (Formula 1). The back-calculation algorithm which is carried out during an FEM simulation includes the extent of the defect in the body to be investigated. If the defect has an extent, this can lead to the position of the defect determined using the sensed magnetic fields and the geometric position of the defect in the body to be investigated differing from one another. This discrepancy is taken into account in the back-calculation algorithm and is therefore compensated for.

The surface of the elongated body with the defect to be investigated also influences the eddy current induced in the body to be investigated. If the defect to be detected is located close to the surface of the body to be investigated, the eddy current can no longer flow over the defect without any impediment. This changes the signal detected by the magnetic field sensors. The FEM simulation for determination of the position of a defect includes the change in an eddy current resulting from the proximity of a fault to the surface of the body to be investigated.

The current density in the body to be investigated and the conductivity of the fault to be investigated depend on the excitation frequency of the magnetic field which surrounds the body to be investigated. This effect is also included in the FEM simulations for fault location. The finite element simulation is corrected by comparison of positions of known faults in the body to be investigated and the positions which are calculated with the aid of the FEM simulation.

FIG. 33 shows a cross section through a wire with curved lines which are calculated for a specific amplitude ratio in an FEM simulation. The shape of the lines differs considerably from the crosswire for geometric determination of the fault position from measured amplitude ratios. In contrast to the mathematical model, no straight amplitude bands or amplitude lines are obtained. The amplitude lines 88, 89 are curved. The lines 88, 89 result, like the straight lines in the mathematical model within the body to be investigated, in an intersection 90 as the position of the fault.

If two magnetic field sensors which are each opposite with respect to the center point of a wire cross-sectional plane are used to determine amplitude ratios, then the position of the fault is obtained from an FEM representation of the measured amplitude ratios as a function of the cross-sectional coordinates of the wire (amplitude map). The amplitude ratios are calculated as an amplitude map in an FEM simulation. For given amplitude ratios, the position of the fault depends on the wire diameter and the excitation frequency of the magnetic field surrounding the wire. When there are a multiplicity of different wire diameters, the calculation of amplitude maps for each individual wire diameter leads to a large amount of effort. The calculation effort can be reduced, however, by not carrying out an FEM simulation for every possible wire diameter. Furthermore, FEM simulations are carried out only for specific excitation frequencies. An interpolation process is used between cut-out simulated wire diameters and excitation frequencies.

The interpolation between two calculated wire diameters and excitation frequencies is carried out using a non-linear fit with a second-order polynomial. The missing amplitude ratios can be determined as a function of the cross-sectional coordinates of the body to be investigated by means of the second-order polynomial between values which are available for the closest wire diameters and excitation frequencies.

FIG. 34 shows the measurement of a signal shift caused by an inclusion in a wire. The illustration of the measurement data in the form of a graph is a function of the angle position of the magnetic field sensor with respect to the inclusion on the cross-sectional plane of the body to be investigated. The excitation frequency is 10 kHz and the wire diameter is 1.4 mm. The measurement data originates from a defect close to the surface, which runs directly under the magnetic field sensor at an angle position of about 210°. The maximum magnetic field signal is detected at an angle position of 210°.

The form of the measurement data 91 allows a good approximation with a Lorenz function. The position of the defect to be measured can be determined by means of a Lorenz fit. FIG. 35 shows, in the form of a graph, data relating to the Lorenz fit simulation in relation to faults at different positions in the wire. These positions can be found in the schematic illustration of a wire cross section in FIG. 36. The magnetic field sensor 62 is arranged directly above the fault 92 on the surface of the wire. Further faults 96 are arranged at a decreasing distance from the wire axis, underneath the fault 92. The simulated measurement data 93 relating to the fault 92 is shown in FIG. 35 as a function of the angle 95 of the magnetic field sensor 62 on the cross-sectional plane of the wire. The Lorenz fit simulation 97 relating to the fault 96 shows, in comparison to the data 93 relating to the fault 92, that lower signal strengths are measured by the magnetic field sensor 62 for defects located deeper in the wire. The position of the magnetic field sensor 62 in the wire cross section, which is shown in FIG. 36, corresponds to an angle position of 90° in FIG. 35.

FIG. 37 shows normalized graphs for the data illustrated in FIG. 35. The signal width 98 increases with the depth of the defect. The defect can be located by the angle position of the maximum, the signal width and the signal level of the Lorenz fit. The Lorenz function is, in a general form:

$$B = a \cdot \left( \frac{\omega}{(\rho - \rho_0^2) + \omega^2} \right) \quad (2)$$

where B is the simulated magnetic field, a is the maximum magnetic field, $\rho_0$ is the angle position of the maximum magnetic field, and $\omega$ is the 3 dB width of the Lorenz function.

The approximation or Lorenz function to the measurement data can be produced, for example, over eight support points between an angle position of 40° and 350° (see FIG. 35). The fault is located by analysis of the fit parameters $\rho_0$, $2\omega$ and $a/\omega$. The position of the maximum of the magnetic field $\rho_0$ indicates the angle between the fault and the magnetic field sensor on the cross-sectional planes of the body to be investigated. The signal width $2\omega$ indicates the depth of the fault. The signal level $a/\omega$ can be used to determine the size of the fault.

The fit using a Lorenz function can be improved by using measurement data from more than four sensors, which are at a distance from one another, for the approximation of the Lorenz function to the measurement data. The position of a fault can be determined by matching a Lorenz function to existing measurement data. The position of a fault can also be determined by evaluation of amplitudes or variables derived from amplitudes (see FIG. 33), or by means of phase information (FIG. 32). Provision is therefore made for characteristic features of the strength, form and phase angle of the signals of magnetic fields sensed by different magnetic field sensors to be used to determine the position and size of a fault. It is also possible to determine the number of faults in an elongated body from the number of peak values in the magnetic fields sensed by the magnetic field sensors. The distance of the fault from the surface of an elongated body can be determined from the phase angle of the sensed magnetic fields. The size or dimensions of the fault can be calculated from the amplitude or from a variable derived from the amplitude of the sensed magnetic fields.

Figure 38:
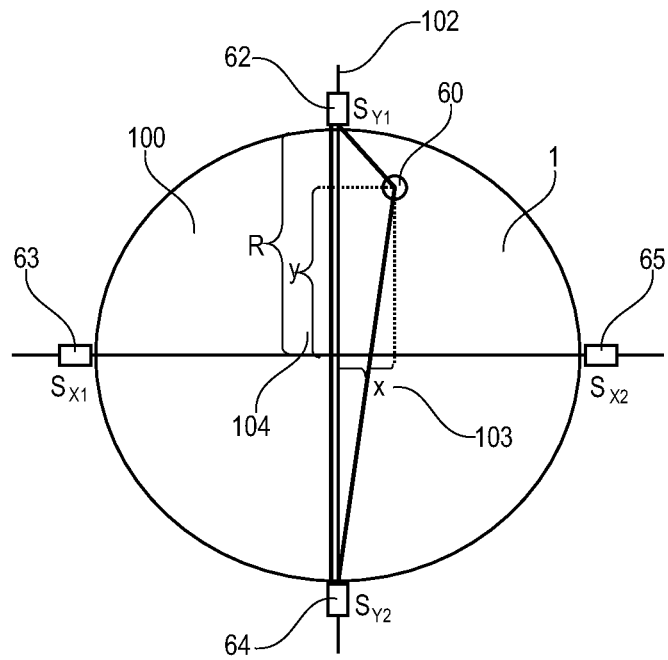
FIG. 38 shows the wire cross section and a test arrangement with four magnetic field sensors for determining the position of a fault in the wire.

FIG. 38 shows, schematically and in the form of a cross section, a wire 1 with a fault 60 and four sensors 62 to 65 which are arranged in the form of a ring around the wire 1. The sensors 63 and 65 are located opposite with respect to the wire center point and form an x-axis 101. The mutually opposite sensors 62 and 64 form a y-axis 102 which is at right angles to the x-axis. The radius 100 of the wire 1 is the distance between the center point of the cross-sectional plane of the wire 1 and each of the sensors 62 to 65. A fault 60 is at a distance from the center point of the cross-sectional plane of the wire 1 with a value of x(103), on the x-axis 101. The fault 60 is at a distance from the center point of the cross-sectional plane of the wire 1 with the value y(104) on the y-axis 102. The XMR sensors (AMR, GMR) that are used are sensitive in only one direction. The sensors 62 to 65 are aligned towards the center point of the wire 1. By way of example, the sensor 62 does not measure the direct connection between the fault 60 and the sensor 62 as the distance to the fault 60. In fact, the magnetic field sensor 62 "sees" the fault 60 only at a distance r(100)−y(104). The sensor 64 opposite the sensor 62 measures only the distance r(100)+y(104) as the distance to the fault 60. In a corresponding manner, the sensor $S_{x1}$(63) measures a distance to the fault 60 of r(100)+x(103), and the sensor $S_{x2}$ measures a distance to the fault 60 of r(100)−x(103). If the magnetic field amplitude $B_{x1}$ of the sensor 63 is related to the magnetic field amplitude $Bx_2$ of the sensor 65, then:

$$b_{x1x2} = \frac{B_{x1}}{B_{x2}} = \frac{z_{x2}^2}{z_{x1}^2} = \frac{(r-x)^2}{(r+x)^2}, \quad (3)$$

where $b_{x1x2}$ is the ratio of the magnetic field amplitudes $B_{x1}$ to the magnetic field amplitude $B_{x2}$. $z_{x1}$ is the distance between the sensor $S_{x1}$(63) and the fault 60. $z_{x2}$ is the distance between the sensor $S_{x2}$ (65) and the fault 60.

According to Formula 1, the measured magnetic field of the sensors 63, 65 is inversely proportional to the square of the distance between the sensors 63, 65 and the fault 60. If the amplitude ratio $b_{x1x1}$ is known, the coordinate x(103) can be calculated from Formula 3. After conversion of Formula 3, this results in a quadratic equation which has two solutions $x_{1/2}$:

$$x_{1/2} = \lambda R \pm \sqrt{(\lambda R)^2 - R^2}, \quad (4)$$

where $\lambda = \left(\frac{1+b_{x1x2}}{1-b_{x1x2}}\right)$ and $b_{x1x2} = B_{x1}/B_{x2}$.

One of the two solutions $x_{1/2}$ will be located outside the wire 1 to be investigated. The coordinate x(103) is therefore uniquely determined via a measured amplitude ratio using the Formula 4. An amplitude ratio can be determined for the sensors 62, 64 in the same way as for the sensors 63, 65 and can be used to calculate the coordinate y(104) of the fault 60. The coordinates x(103) and y(104) form the intersection 90 of the amplitude map calculated using an FEM simulation as shown in FIG. 33.

The position of a fault 60 on the cross-sectional plane of a wire 1 can be calculated using Formula 4, if a signal from the fault 60 is measured by each of the four sensors 62 to 65. This results in two amplitude ratios of the respectively opposite sensors and lines 88, 89 are determined by means of the FEM-simulated amplitude maps. The intersection 90 of the lines 88, 89 corresponds to the position of the fault 60.

This back-calculation algorithm can be adapted if one or more of the four sensors 62 to 65 does not register any defect signal. The magnetic field sensor(s) without any defect signal emits or emit a signal in the form of sensor noise to the lock-in amplifier 14. The defect signal has the sensor noise superimposed on it. The defect signal to be measured from the noisy magnetic field sensor is less than or equal to the signal which is measured as noise. For example the sensor $S_{x1}$ measures a magnetic field amplitude of 100 µT. The sensor $S_{x2}$ measures only noise with a value of, for example, 30 nT. The amplitude ratio of the two sensors is:

$$b_{x1x2} \geq \frac{B_{x1}}{B_{x2}} = \frac{100\mu T}{30 nT} \Rightarrow B_{x1x2} \geq 3300. \quad (5)$$

Figure 39:
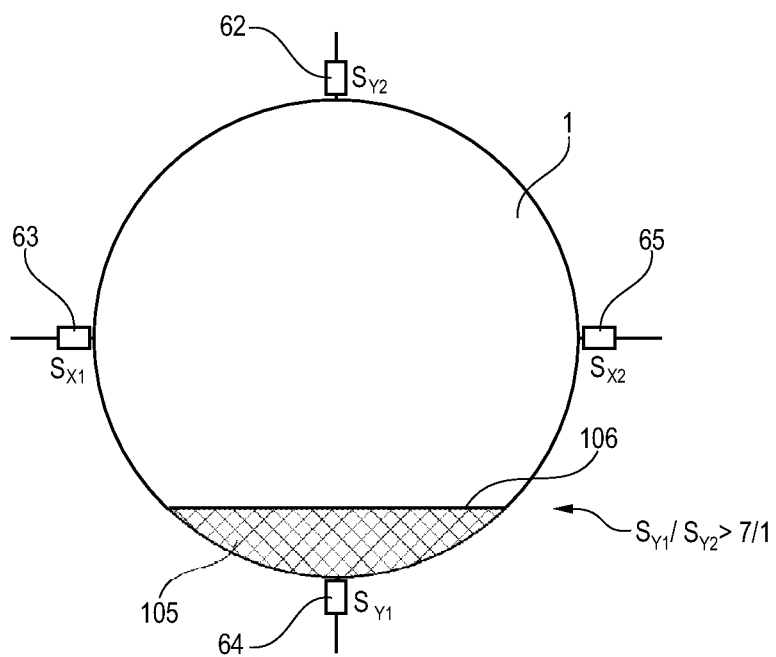
FIG. 39 shows, schematically, an area in a wire cross section in which a fault is located with the area being calculated inter alia with the aid of measured values which are not caused by the fault, of a sensor in the test arrangement shown in FIG. 38.

An area 105 which is illustrated schematically in FIG. 39 is obtained from a curved amplitude line or an amplitude band 88, 89. The sensor 64 measures a noise signal in which the signal is submerged in the interference. The area 105 indicates the area in the cross section of the wire 1 in which the fault must be located in the y-direction in the case of amplitude ratio formation from the sensors 62, 64. The area on the cross-sectional plane of the wire 1 outside the area 105 indicates the area of a defect in which the defect would produce a measurement signal at the magnetic field sensor 64 of greater than or equal to 30 nT. The defect can therefore not be located outside the area 105 in the wire 1. The sensors 62, 64 are sensitive only in the direction of the y-axis. The area 105 is therefore bounded by a straight line 106 which is arranged at right angles to the connecting line between the sensors 62, 64. The area 105 on the cross section of the wire 1 is bounded by the line 106, which is defined by the amplitude ratio 3300.

In addition to the sensor 63, the sensors 62 and 64 register a measurement signal from the fault to be detected. A line 88 which can be superimposed on the area 105 is obtained once again from the amplitude ratio of the magnetic fields of the sensors 62, 64. The position of the fault to be detected is located in that area of the line 88 located within the area 105.

If one of the two sensors 63, 65 measures only weak noise in addition to the sensor 64, this results in two areas in each of which the defect must be located. This area is the cut area which is formed by superimposition of the two areas.

An amplitude ratio can also be formed from sensors which are adjacent on the circumference of the wire 1. In the case of the arrangement of the sensors 42 to 45 shown in FIG. 39, only that quarter of the cross-sectional area of the wire 1 which is enclosed by the adjacent sensors is used for determination of the defect positions in the back-calculation algorithm. If there are more than four sensors, the only amplitude ratios of the magnetic fields which are sensed by adjacent magnetic field sensors which are used are those which have cross-sectional coordinates in a segment of the wire cross section. The segment in the wire cross section has two straight lines and a line on the circumference of the wire. The line connects the adjacent sensors by the shortest route. The straight lines of the segment each run through the wire center point and the position of the two adjacent sensors. The information relating to determination of the position of amplitude ratios of adjacent sensors can be combined with the information from mutually opposite sensors. It has been found that intersections between lines from amplitude ratios of sensed magnetic fields of mutually opposite magnetic field sensors and amplitude ratios of sensed magnetic fields of adjacent sensors should not be used to determine the position of a fault.

If the sensors 62 to 65 are arranged as shown in FIG. 38 and there is an adequate signal at all the sensors for the fault to be investigated, this results in two lines from the amplitude ratios of sensors which are opposite with respect to the longitudinal axis of the wire 1, with one intersection. In addition, four lines from the amplitude ratios can in each case be used from sensors adjacent on the circumference of the wire 1, in order to determine the position of the fault, forming four intersections. Overall, the arrangement of the sensors shown in FIG. 39 results in five intersections. The position of a fault determined by measurement is therefore overdefined when using four sensors which each detect a signal produced by a fault. The intersections that are determined are averaged in order to determine the position of the fault.

Measurement of a defect using the test arrangement shown in FIG. 5 leads to a change in the resistance in the resistance strips 22, 23 of each magnetic field sensor that is used. This resistance change in the magnetic field sensor results in a voltage shift. The voltage shift is detected by the lock-in amplifier 14. This voltage shift can be associated with a magnetic field with the aid of the characteristic of the magnetic field sensors. The magnetic field caused by the defect to be investigated can be determined in this way. The magnetic field B is given by:

$$B = \frac{\mu_0 j_0}{1.354}\left(\frac{\beta-1}{\beta+2}\right)\frac{r^3}{z^2} \quad (6)$$

where $\mu_0 = 4\pi \cdot 10^{-7}$ N/A$^2$ and $j_0$ is the eddy current density at the position of the fault in the wire, $\beta = \sigma_{Def}/\sigma_{Mat}$ is the ratio of the conductivity of the fault $\sigma_{Def}$ to the conductivity $\sigma_{Mat}$ of the wire without a fault, z is the distance between the center point of the fault and a magnetic field sensor and r is the radius of the fault.

The eddy current density $j_0$ at the position of the fault in the wire is calculated by means of an FEM simulation. Formula 1 can be used to determine the position of the fault to be investigated in the wire, on the cross-sectional plane of the wire. Alternatively, the position of the fault to be investigated can be determined by superimposition of phase bands, as shown in conjunction with FIG. 32. The ratio of the conductivity of the fault $\sigma_{Def}$ to the conductivity of the wire without a fault $\sigma_{Mat}$ can be determined experimentally. If the position of the fault in the wire is known, the distance between the center point of the fault and each magnetic field sensor that is present can be calculated from the cross-sectional coordinates of the fault in the wire.

The radius of the fault is varied in the back-calculation algorithm such that the calculated absolute value of the magnetic field corresponds to each of the sensed absolute values of the magnetic fields of the magnetic field sensors which are present. The fault diameters calculated from the absolute values of the sensed magnetic fields of each magnetic field sensor may differ from one another. In this case, the position of the fault is varied in an iterative procedure. The iteration is ended when the diameters calculated from the absolute values of each magnetic field sensor match or the diameters differ little from one another. Values of amplitudes can be used as absolute values of the sensed magnetic fields.

Figure 40:
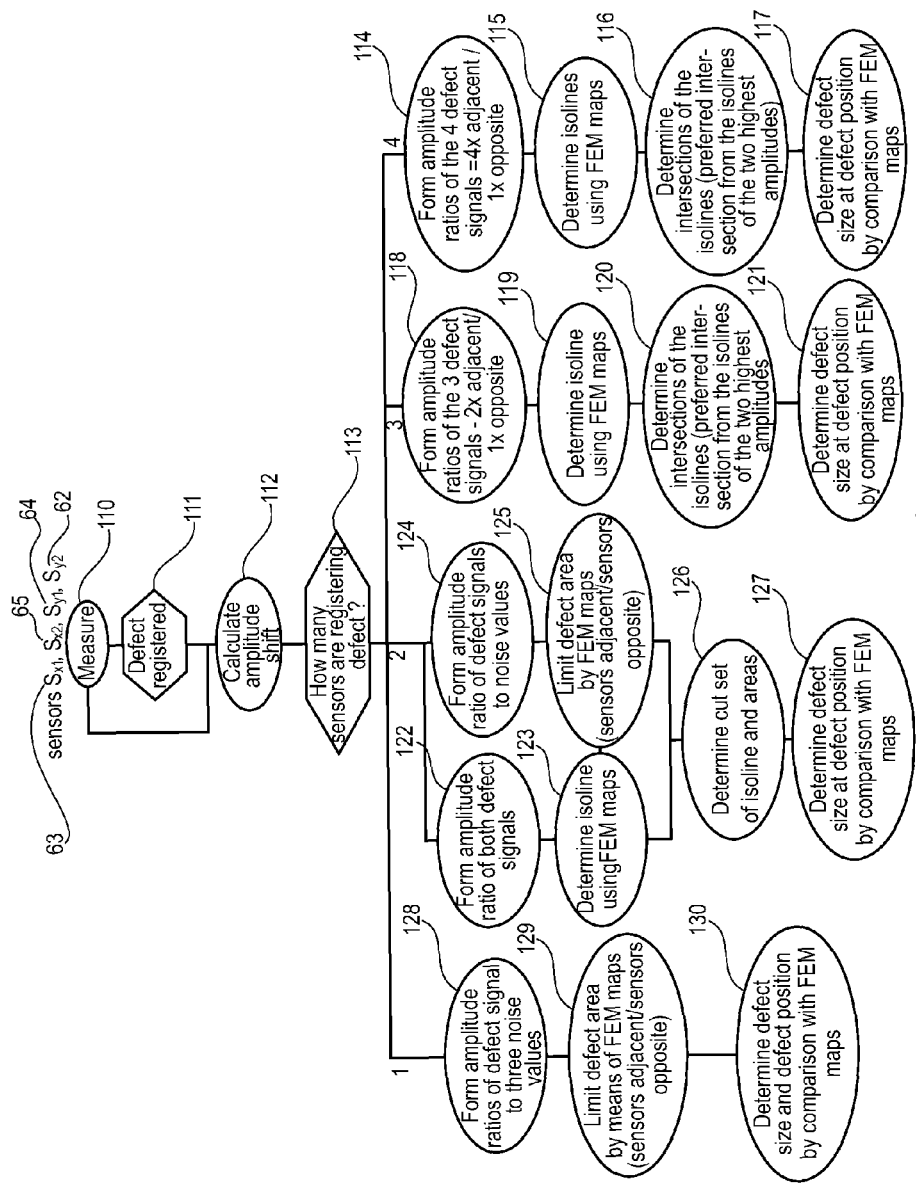
FIG. 40 shows a flowchart, for various options for determination of the defect position and defect size when sensor information is lacking.

A flowchart, which shows the process for determining the defect position and defect size when magnetic field sensor information is lacking, is shown in FIG. 40. Signals are sensed by the sensors 62 to 65 (110), starting from the arrangement of the sensors as shown in FIG. 39. As long as there are no measurement signals, no defect is registered (111). The data from the sensors 62 to 65 is not stored in the evaluation unit 19. If a defect is registered, the signal shift 68 of the amplitude of the magnetic field sensor is calculated (112) for each magnetic field sensor. This is followed by confirmation of the number of sensors which have registered a defect (113). If measurement signals are present from all four sensors, the amplitude ratios are formed in each case for mutually opposite sensors and adjacent sensors (114). This results in four amplitude ratios for adjacent sensors. In addition, two amplitude ratios are obtained from opposite sensors. Lines 88, 89 are formed on the cross-sectional plane of the body to be investigated (115) by means of FEM simulation, using the available amplitude ratios. The intersections of the lines of mutually opposite sensors and the intersections of the lines of adjacent sensors are now formed. The intersection is preferably formed from the lines which are formed from the amplitude ratios of the two greatest measured amplitudes (116). If the defect position is known, the distance from the defect to each magnetic field sensor can be determined by FEM simulation. The defect size is calculated in the evaluation unit 19 using the Formula 6 (117).

When three sensors register a defect, the amplitude ratios of the signals are formed from three magnetic field sensors (118). This results in two amplitude ratios from adjacent sensors and one amplitude ratio from mutually opposite sensors. In addition, amplitude ratios are obtained from the inequalities with the magnetic field sensors which measure only weak noise. An intersection is obtained from the two lines of the amplitude ratios of adjacent sensors. The line from the amplitude ratios of mutually opposite sensors additionally can be used to determine the position. In addition, areas occur which are formed from the amplitude ratios with sensors which measure only weak noise. The defect is located within the cut area of the areas calculated by means of inequalities. The position problem is therefore adequately defined (120) for three sensors which detect a defect. The intersection is preferably determined from the lines which are determined from amplitude ratios with the greatest measured amplitudes. Once the position of the defect has been determined, the defect size can be calculated using Formula 5 (121).

When two sensors register a defect, only the amplitude ratios of adjacent sensors are considered. If the amplitudes were to originate from mutually opposite sensors, the adjacent sensors would also have to detect the defect to be detected. This confirms that the defect is located in that quadrant of the cross-sectional area of the wire enclosed by the adjacent sensors. The amplitude ratio of the two sensors which register a defect is then formed (122). This amplitude ratio is used to determine a line by means of an FEM simulation on the cross-sectional area of the wire (123). In addition, the amplitude ratios which each contain a defect signal and a noise signal in the denominator are formed (124). Areas 105 to demark the position of the defect are obtained from the inequalities relating to the amplitude ratios of mutually opposite sensors. In addition, areas which allow demarcation of the position of the fault (125) are obtained from the inequalities of the amplitude ratios with adjacent sensors. The line from the amplitude ratio of the sensors which register a defect is superimposed on the areas from amplitude ratios with magnetic field sensors which produce only a noise signal. In most cases, the position of a defect can be determined even if the position problem is mathematically underdefined (126). The defect size is determined using the Formula 6 (127) using the position of the defect. The defect has a small extent if only two sensors register a defect since, if the defect had a large extent, all four sensors would have to emit a signal registering the defect to the lock-in amplifier 14.

If there is only one sensor registering a defect, the amplitude ratios are formed from amplitudes which include this sensor. This results in three amplitude ratios (128). The three amplitude ratios result in three areas within the cross-sectional area of the wire. A cut area is obtained by superimposition of areas of adjacent sensors. This cut area can be superimposed on the area from the inequality of the amplitude ratios of the sensed magnetic fields of magnetic field sensors which are opposite the wire center point. This allows demarcation of the position of the defect (129).

The distance between the fault to be detected and the sensor which registers a defect is considerably less than that to the three other sensors. The maximum size of the fault in the wire can also be achieved by absolute matching of the measured amplitude ratios with amplitude ratios determined in an FEM simulation as a function of the cross-sectional coordinates. The measured amplitude ratios which are used are those amplitude ratios which contain in the denominator magnetic field amplitudes sensed by magnetic field sensors which produce only a weak noise signal. The distance of the defect from the sensor which registers a defect can be estimated (129) from the inequality of the ratio of amplitudes from mutually opposite sensors. This distance can be used to determine the defect size by means of Formula 6 (130). Up to a signal-to-noise ratio of 20, the size of the fault in the wire can be determined for the magnetic field amplitudes of the magnetic field sensors with only weak noise.

If only one sensor detects a defect, the defect is located in a specific area within the wire. This area describes a circular ring with a minimal internal radius. This radius corresponds to a minimal distance to the center point of the wire cross-sectional plane on which the fault is located. The outer boundary of the circular ring is formed by the wire radius. A maximum defect size can be indicated by the minimal internal radius. However, the defect need not be located on the minimal internal radius. If it is located further outwards, then the defect radius must be smaller. If the defect radius were to be larger, the sensor measuring the defect would have to register a larger signal. The considerations relating to only one sensor registering a defect can be transferred to two sensors registering a defect. When two sensors register a defect, it is advantageous that the position of the defect can be restricted to the cross-sectional plane of the wire in the x-direction and y-direction. When forming amplitude ratios with amplitudes from sensors with only weak noise, the amplitudes of these magnetic field sensors are advantageously located in the denominator.

After being measured by four GMR sensors, a wire 1 is tested destructively, and the position and size of the defect 60 is determined. The wire 1 is rotated about the wire axis in 10° steps and four GMR sensors each measure it after each rotation. The defect position is then determined. FIG. 41 shows the defect position for different angle positions, as measured in the respective angle positions of the fault by the GMR sensors. The defect radii calculated by means of the positions illustrated in FIG. 41 are illustrated in FIG. 42. The defect 60 is indicated independently of the angle position of the sensors with respect to the defect in the correct quadrant of the wire cross section. The defect position is dependent on the angle position of the sensors with respect to the defect. The shortest distance between the defect and the wire center point is reached at an angle position of about 40° (13). The defect radius is approximately 40 μm, with a good match over all four sensors. For a given angle position of the defect with respect to the four sensors and with the defect radii 136, 137, 138 being averaged over all the magnetic field sensors, the defect radius is virtually independent of the angle position of the defect with respect to the measurement arrangement.

FIG. 43 shows, schematically, a current distribution in a wire 1 with a filament structure 61. The wire 1 has a "thick core" 140 and a defect 141. The defect zone of the defect 141 has a length of 400 μm. The diameter of the "thick core" is three times as great as the diameter of a filament of the filament structure 61.

Figure 44:
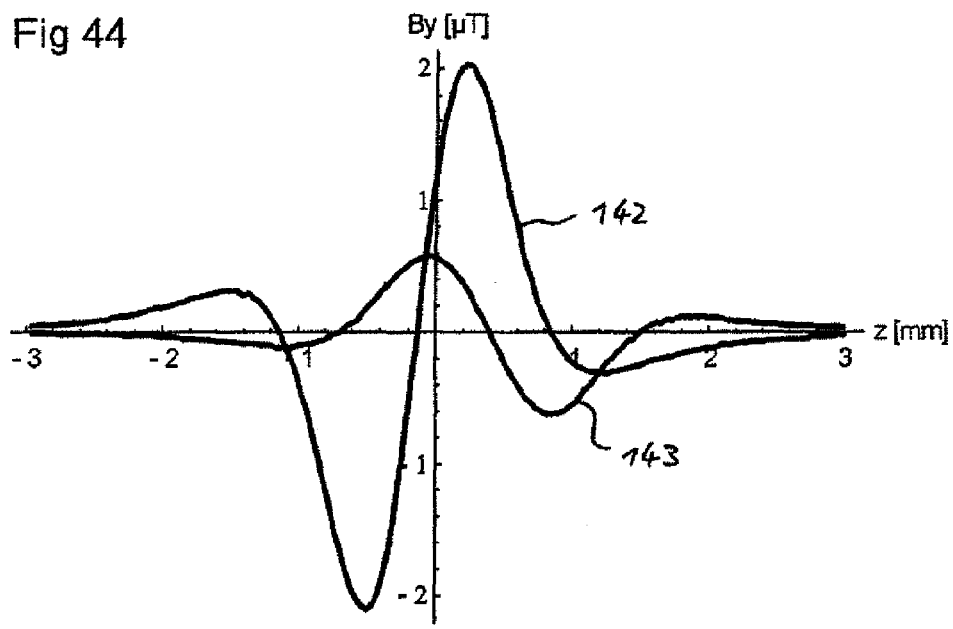
FIG. 44 shows an illustration in the form of a graph of the signal strength of magnetic fields of the defect and of the thick core in the superconducting wire shown in FIG. 43.

FIG. 44 shows, in the form of a graph, the field distribution of a signal from the defect 141 and of a signal from the "thick core" 140 of the superconducting wire 1. The signal 142 from the "thick core" 140 exhibits a reversal in the measured field amplitudes in comparison to the signal 143 from the defect 141. It is therefore possible to distinguish from the profile of the measurement signals between a defect and a "thick core" in the filament structure 61 of a superconducting wire 1.

The profiles of the signals from the sensors 62 to 65 as shown in FIGS. 21 to 23 show that the signal length 67 is dependent on the angle between the fault and the measuring sensor on the cross-sectional plane of the wire 1. The signal length increases with an increasing angle between the fault 60 and the sensor on the cross-sectional plane of the wire 1. FIG. 45 shows the signal length 145 to 148 for four different wires as a function of the angle position of the defect. This shows a maximum signal length 67 for an angle position of the defect to be investigated with respect to the magnetic field sensor of 180° irrespective of the wire used. Defects with short dimensions in the direction of the wire 1 have shorter signal lengths than defects with long dimensions in the direction of the wire axis. Defects with small dimensions at right angles to the wire direction have a faster rise in the signal width at a higher angle position than defects with larger dimensions at right angles to the wire direction.

FIG. 46 shows, in the form of a graph, the signal length 67 of the defect signals from four sensors 62 to 65, which are arranged in the form of a ring around the wire 1, as a function of the defect length. As is shown in FIG. 20, one defect 60 runs directly under the sensor 62, and past it. The signal width 151 of the sensor 62 is considerably less than the signal width 152, 154 of the sensors 63, 65. The signal from the sensor 64 has the greatest signal width 153. The position of the sensors 62 to 65 leads to four angle positions of the sensors with respect to the defect to be investigated. Measurement data relating to four different angle positions is therefore available for one defect. As shown in FIG. 46, the defect length 150 increases linearly with the signal width 67.

The signal length 67 can be determined for each magnetic field sensor 62 to 65 as the interval between a minimum and a maximum in the signal from a defect in the wire. The position of the fault in the wire 1 can be determined by means of amplitude ratios and/or phase information in the defect signal. The angle of each magnetic field sensor with respect to the fault can be determined from the position of the fault. The length of a fault 150 in the wire 1 in the direction of the wire can be determined as a function of the signal length 67 from a sensor. The signal length is dependent on the angle between the sensor and the position of the fault.

FIG. 46 shows an example of the linear relationship between the defect length 150 and the signal width 67. A defect length 150 can be determined in each case for each magnetic field sensor from the signal length 67 for a calculated angle between the magnetic field sensor and the position of the fault in the wire 1. When there are four magnetic field sensors, there are four defect lengths 150 relating to a fault to be investigated. The defect lengths 150 relating to a fault can be averaged. The defect length 150 can be determined by averaging over four defect lengths, with an accuracy of about ±15%.

The invention claimed is:

1. An arrangement designed for testing a wire or a welded or bonded joint in the wire for faults, comprising:
    a device for production of an eddy current in the wire or the welded or bonded joint, and at least two magnetic field sensors for sensing the magnetic field on the wire or the welded or bonded joint, and
    an evaluation unit configured to indicate a phase angle, amplitude, signal length and a number of peak values from data relating to the sensed magnetic field as characteristics of a fault in the wire;
    wherein the at least two magnetic field sensors are located symmetrically with respect to one another, with respect to a cross-sectional center point of the wire.

2. The arrangement as claimed in claim 1, in which an array comprising at least four magnetic field sensors is arranged in an annular shape around the wire.

3. The arrangement as claimed in claim 1, having an evaluation unit which is designed to process amplitudes and phase information and/or real and imaginary parts of the sensed magnetic fields.

4. The arrangement as claimed in claim 3, in which the evaluation unit has a multichannel lock-in amplifier which is designed to read measurement data from a plurality of magnetic field sensors simultaneously.

5. The arrangement as claimed in claim 1, in which the magnetic field sensors are in the form of anisotropic magneto-resistance (AMR) sensors or an AMR sensor array having a multiplicity of individual sensors.

6. The arrangement as claimed in claim 1, in which the magnetic field sensors are in the form of a giant magneto-resistance (GMR) sensor or a multiplicity of GMR sensors.

7. The arrangement as claimed in claim 1, furthermore having at least one gradiometric excitation coil.

8. The arrangement as claimed in claim 2, in which in each case two magnetic field sensors, which are opposite with respect to the center point of the wire, are offset with respect to one another in the direction of the axis of the wire.

9. The arrangement as claimed in claim 1, in which the position of the magnetic field sensors around the wire is determined by means of at least one manipulator.

10. The arrangement as claimed in claim 1, in which the magnetic field sensors are each sensitive to the magnetic field to be sensed in only one direction.

11. A method for testing a wire or a welded or bonded joint in the wire for faults, comprising:
    producing a current in the wire or the welded or bonded joint and sensing the magnetic field on the wire or the welded or bonded joint and
    sensing the magnetic field on the wire or the welded or bonded joint by means of at least two magnetic field sensors, wherein the at least two magnetic field sensors are located at opposite circumferential locations of the wire;
    wherein a phase angle, amplitude, signal length and a number of peak values from data relating to the sensed magnetic field are indicated as characteristics of a fault in the wire.

12. The method as claimed in claim 11, in which the phase angles of the magnetic fields measured by the magnetic field sensors are plotted as different lines of equal phase on the basis of the different positioning of a plurality of magnetic field sensors with respect to the wire, and an intersection of the various lines on a bounded surface of the cross section of the wire is determined which corresponds to the location of the fault in the wire.

13. The method as claimed in claim 11, in which the number of faults in the wire is determined by means of the number of peak values in the sensed magnetic field, the distance between the fault and the surface of the wire is calculated from the phase angle of the sensed magnetic field, and the size of the fault is calculated from the amplitude of the sensed magnetic field.

14. The method as claimed in claim 11, in which the processing of the sensed magnetic field comprises the following steps:
    compensation for the movement of the wire at right angles to the longitudinal axis of the wire, wherein the data is set to zero by subtraction of a linear function from the data relating to the sensed magnetic fields, and
    setting of a phase angle in the sensed magnetic field via a phase rotation until the sensed magnetic field of the fault in one channel has an amplitude which is as large as possible in comparison to a compensation signal, wherein amplitudes and phase data are used which are recorded in a lock-in amplifier, and
    compensation for the joint movement of the wire axially with respect to the longitudinal axis of the wire by squaring the sensed magnetic field or a variable which is formed from the sensed magnetic field.

15. The method as claimed in claim 11, in which the position of a fault in the wire is determined on the basis of the phase data of the sensed magnetic field, wherein a single magnetic field sensor for the sensed magnetic field can find the position of the fault at any point in a phase band which is formed from the positions of equal phase on the cross-sectional plane of the wire, on which plane the individual magnetic field sensor is arranged, and
    a further phase band is formed on the cross-sectional plane of the wire for the magnetic field sensed by every other magnetic field sensor and is superimposed on the phase bands of the sensed magnetic fields of the other magnetic field sensors, wherein the phase angle of the sensed magnetic field of each magnetic field sensor is aligned with respect to the wire and with respect to the other magnetic field sensors on the basis of the position of the magnetic field sensors with respect to the wire and with respect to the other magnetic field sensors, and an intersection which corresponds to the position of the fault on the cross-sectional plane of the wire is formed by superimposition of the phase angles of the sensed magnetic fields of different magnetic field sensors.

16. The method as claimed in claim 11, in which in order to determine the position and size of faults in a wire, the relationships are evaluated between amplitudes which are formed from amplitudes of the sensed magnetic fields from magnetic field sensors which are opposite with respect to the wire longitudinal axis and are adjacent, wherein an array comprising at least four magnetic field sensors is positioned in an annular shape around the wire to be tested, wherein the ring forms a plane which runs at right angles to the longitudinal axis of the wire and each magnetic field sensor is arranged at the same distance from adjacent magnetic field sensors on the circumference of the wire, wherein each of the at least four magnetic field sensors is sensitive to the magnetic field to be sensed in only one direction, wherein the sensitive measurement axis of each magnetic field sensor is at right angles to the wire longitudinal axis and each magnetic field sensor is aligned with its sensitive measurement axis towards the wire longitudinal axis, and the ratio of the amplitudes of the sensed magnetic fields of magnetic field sensors which are opposite with respect to the wire longitudinal axis is formed, wherein only the magnetic field components in the direction of the sensitive measurement axes are sensed as amplitudes of the sensed magnetic fields, and an amplitude ratio of the sensed magnetic fields from magnetic field sensors which are opposite with respect to the wire longitudinal axis is formed and corresponds to a line in the cross section of the wire, and the fault in the wire is located at a point on the line, and an intersection which corresponds to the position of the fault in the wire cross section is formed in the wire cross section by superimposition of two lines which correspond to amplitude ratios of in each case two magnetic field sensors which are opposite with respect to the wire longitudinal axis.

17. A wire testing apparatus, comprising:

a device for production of an eddy current in a wire, at least two magnetic field sensors which are arranged at opposite circumferential locations of the wire, in order to sense a magnetic field which is formed by the eddy current; and an evaluation unit configured to indicate a phase angle, amplitude, signal length and a number of peak values from the data relating to the sensed magnetic field as characteristics of a fault in the wire.

18. The wire testing apparatus as claimed in claim 17, comprising an even number of magnetic field sensors, wherein each sensor pair is arranged opposite with respect to a cross-sectional center point of the wire, and the sensor pairs are arranged offset with respect to one another in the circumferential direction of the wire.

19. The wire testing apparatus as claimed in claim 17, wherein the magnetic field sensors are GMR sensors or AMR sensors with a spatial resolution of approximately 100 μm.

* * * * *